(12) United States Patent
Tada et al.

(10) Patent No.: US 12,086,224 B2
(45) Date of Patent: Sep. 10, 2024

(54) DETECTION DEVICE AND METHOD FOR AUTHENTICATION

(71) Applicant: Japan Display Inc., Tokyo (JP)

(72) Inventors: Masahiro Tada, Minato-ku (JP); Takashi Nakamura, Minato-ku (JP); Akio Takimoto, Minato-ku (JP)

(73) Assignee: Japan Display Inc., Tokyo (JP)

( * ) Notice: Subject to any disclaimer, the term of this patent is extended or adjusted under 35 U.S.C. 154(b) by 311 days.

(21) Appl. No.: 17/444,917

(22) Filed: Aug. 12, 2021

(65) Prior Publication Data

US 2021/0374223 A1 Dec. 2, 2021

Related U.S. Application Data

(63) Continuation of application No. PCT/JP2019/044971, filed on Nov. 15, 2019.

(30) Foreign Application Priority Data

Feb. 19, 2019 (JP) .................................. 2019-027837

(51) Int. Cl.
*G06F 21/32* (2013.01)
*G06F 3/041* (2006.01)
(Continued)

(52) U.S. Cl.
CPC .............. *G06F 21/32* (2013.01); *G06F 3/041* (2013.01); *G06F 3/04883* (2013.01);
(Continued)

(58) Field of Classification Search
CPC ...... G06F 21/32; G06F 3/041; G06F 3/04883; G06F 2203/04808; G06V 40/145; G06V 40/1318; G06V 40/70; G06V 40/14
See application file for complete search history.

(56) References Cited

U.S. PATENT DOCUMENTS

| 2013/0128206 | A1 | 5/2013 | Nakano et al. |
| 2018/0225438 | A1 | 8/2018 | Hama et al. |
| 2020/0260016 | A1* | 8/2020 | Misawa .............. G06F 3/04883 |

FOREIGN PATENT DOCUMENTS

| JP | 2007304646 A | * | 11/2007 |
| JP | 2013-130862 A | | 7/2013 |

(Continued)

OTHER PUBLICATIONS

International Search Report issued Feb. 10, 2020 in PCT/JP2019/044971 filed on Nov. 15, 2019, 6 pages (with English Translation).

(Continued)

*Primary Examiner* — Ayoub Alata
(74) *Attorney, Agent, or Firm* — Maier & Maier, PLLC

(57) ABSTRACT

A detection device comprising: an input unit configured to receive an operation of a user; a biosensor provided on the input unit and configured to detect biological information on the user; a position sensor configured to detect an operating position that is a position on the input unit where the user has performed the operation; and a controller, wherein the controller comprises: an operation determination unit configured to determine, based on the operating position detected by the position sensor, whether the user has operated the input unit along a predetermined trajectory; and a biological information acquirer configured to, when the user is determined to have operated the input unit along the predetermined trajectory, acquire, from the biosensor, the biological information on the user when the user has operated the input unit along the predetermined trajectory.

3 Claims, 15 Drawing Sheets

(51) Int. Cl.
*G06F 3/04883* (2022.01)
*G06V 40/13* (2022.01)
*G06V 40/145* (2022.01)
*G06V 40/70* (2022.01)
*G06V 40/14* (2022.01)

(52) U.S. Cl.
CPC ........ *G06V 40/1318* (2022.01); *G06V 40/145* (2022.01); *G06V 40/70* (2022.01); *G06F 2203/04808* (2013.01); *G06V 40/14* (2022.01)

(56) References Cited

FOREIGN PATENT DOCUMENTS

| | | | |
|---|---|---|---|
| JP | 2017-033499 A | 2/2017 | |
| JP | 2018-128785 A | 8/2018 | |
| JP | 2018-169820 A | 11/2018 | |
| JP | 2018-170747 A | 11/2018 | |
| JP | 2018-185825 A | 11/2018 | |
| WO | WO-2008062544 A1 * | 5/2008 | ......... G06K 9/00033 |

OTHER PUBLICATIONS

Office Action issued on Nov. 8, 2022, in corresponding Japanese Application No. 2019-027837, 7 pages.
Office Action issued on Jun. 13, 2023, in corresponding Japanese Application No. 2019-027837, 5 pages.

* cited by examiner

DETECTION DEVICE AND METHOD FOR AUTHENTICATION

CROSS-REFERENCE TO RELATED APPLICATION

This application is a continuation of PCT international application No. PCT/JP2019/044971 filed on Nov. 15, 2019 which designates the United States, incorporated herein by reference, and which claims the benefit of priority from Japanese Patent Application No. 2019-027837 filed on Feb. 19, 2019, incorporated herein by reference.

BACKGROUND

1. Technical Field

The present invention relates to a detection device and a method for authentication.

2. Description of the Related Art

To limit access to an electronic device, the electronic device is sometimes provided with an authentication system. For example, Japanese Patent Application Publication Laid-open No. 2017-033499 describes that a touchscreen panel is provided with a sensor for detecting biological information on a user, and the user is authenticated based on the biological information.

When the sensor is used to detect the biological information on the user, a finger, for example, needs to be made proximate to the touchscreen panel. However, depending on the state of proximity of the finger, the biological information on the user may not be appropriately detected. Therefore, the biological information on the user is required to be appropriately detected.

The present invention has been made in view of the above-described problem, and aims to provide a detection device capable of appropriately detecting the biological information on the user and a method for authentication.

SUMMARY

A detection device according to an embodiment of the present disclosure includes an input unit configured to receive an operation of a user, a biosensor provided on the input unit and configured to detect biological information on the user, a position sensor configured to detect an operating position that is a position on the input unit where the user has performed the operation, and a controller. The controller includes an operation determination unit configured to determine, based on the operating position detected by the position sensor, whether the user has operated the input unit along a predetermined trajectory, and a biological information acquirer configured to, when the user is determined to have operated the input unit along the predetermined trajectory, acquire, from the biosensor, the biological information on the user when the user has operated the input unit along the predetermined trajectory.

A method for authentication of a user according to the present disclosure is disclosed. The method using a detection device includes an input unit configured to receive an operation of a user, a biosensor provided on the input unit and configured to detect biological information on the user, and a position sensor configured to detect an operating position that is a position on the input unit where the user has performed the operation. The method includes an operation determining step of determining, based on the operating position detected by the position sensor, whether the user has operated the input unit along a predetermined trajectory, and a biological information acquiring step of, when the user is determined to have operated the input unit along the predetermined trajectory, acquiring, from the biosensor, the biological information on the user when the user has operated the input unit along the predetermined trajectory.

DETAILED DESCRIPTION

Figure 1:
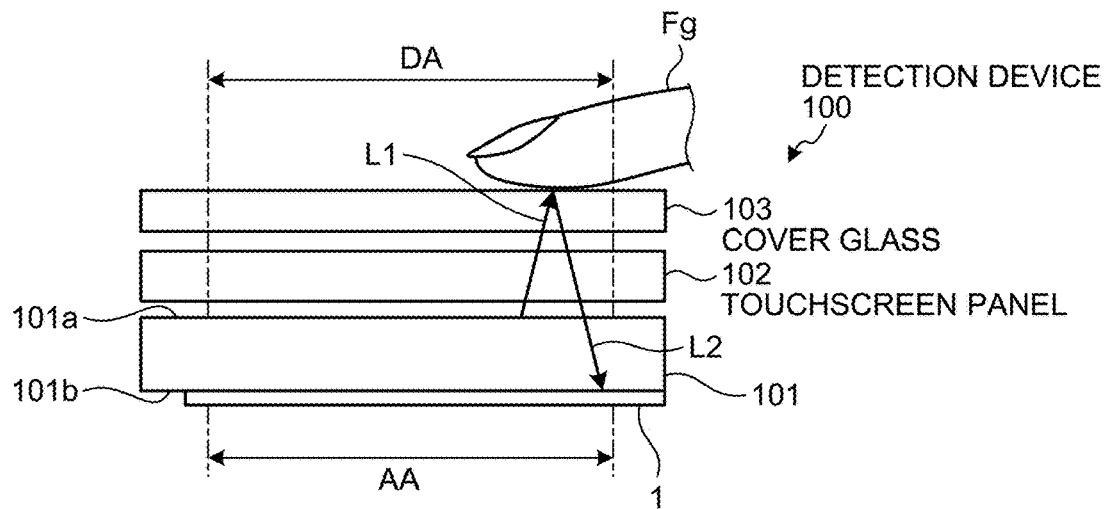
FIG. 1 is a sectional view illustrating a schematic sectional configuration of a detection device according to an embodiment of the present invention.

The following describes an embodiment for carrying out the present invention in detail with reference to the drawings. The present invention is not limited to the description of the embodiment given below. Components to be described below include those easily conceivable by those skilled in the art or those substantially identical thereto. Moreover, the components to be described below can be appropriately combined. What is disclosed herein is merely an example, and the present invention naturally encompasses appropriate modifications easily conceivable by those skilled in the art while maintaining the gist of the invention. To further clarify the description, the drawings schematically illustrate, for example, widths, thicknesses, and shapes of various parts as compared with actual aspects thereof, in some cases. However, they are merely examples, and interpretation of the present invention is not limited thereto. The same element as that illustrated in a drawing that has already been discussed is denoted by the same reference numeral through the description and the drawings, and detailed description thereof will not be repeated in some cases where appropriate.

Overall Configuration of Detection Device FIG. 1 is a sectional view illustrating a schematic sectional configuration of a detection device according to the present embodiment. A detection device 100 according to the present embodiment is a display device capable of detecting biological information on a user. As illustrated in FIG. 1, the detection device 100 includes a biological information detection device 1, a display panel 101, a touchscreen panel 102, and a cover glass 103. The biological information detection device 1, the display panel 101, the touchscreen panel 102, and the cover glass 103 are provided so as to overlap one another in the detection device 100.

The display panel 101 includes a plurality of display elements for displaying an image, and may be, for example, an organic electroluminescent (EL) (organic light-emitting diode (OLED)) display panel or an inorganic EL (micro-LED or mini-LED) display that uses light-emitting elements as the display elements. Alternatively, the display panel 101 may be a liquid crystal display (LCD) panel that uses liquid crystal elements as the display elements, or an electrophoretic display (EPD) panel that uses electrophoretic elements as the display elements.

The display panel 101 has a first principal surface 101a and a second principal surface 101b on the opposite side of the first principal surface 101a. The first principal surface 101a is a display surface on which the image is displayed, and emits light L1 from the display elements of the display panel 101 and a light source unit toward the cover glass 103. The first principal surface 101a has a display area DA in which the image is displayed.

The touchscreen panel 102 is provided on the first principal surface 101a of the display panel 101. The touchscreen panel 102 is an input unit for receiving operations of the user. The touchscreen panel 102 uses, for example, a capacitance method to detect a finger Fg or a palm of the user in contact with or in proximity to a surface of the cover glass 103. Hereinafter, unless otherwise noted, the term "proximity" refers to a case where the finger Fg or the palm is in contact with the surface of the cover glass 103, or a case where the finger Fg or the palm is close to the surface of the cover glass 103 to such an extent that the biological information or a position of the finger Fg or the palm is detectable.

The touchscreen panel 102 includes a position sensor 10A (refer to FIG. 3), and uses the position sensor 10A to detect the position of the finger Fg or the palm of the user in proximity to the surface of the cover glass 103, that is, coordinates of the position in the display area DA of the display panel 101 in proximity to the finger Fg or the palm. Hereinafter, the term "operating position" refers to the position in the display area DA of the display panel 101 in proximity to the finger Fg or the palm that is detected by the position sensor 10A. The operating position can be said in other words as a position (coordinates) on the touchscreen panel 102 where the user has performed an operation. The position sensor 10A is configured by providing, for example, a plurality of pairs of opposed electrodes in a matrix having a row-column configuration in the display area DA. However, any configuration can be employed as long as the sensor can detect the operating position.

The touchscreen panel 102 is translucent, and can transmit the light L1 and reflected light L2. The light L2 includes light reflected on an interface between the cover glass 103 and air, and light reflected on a surface of the finger Fg. The display panel 101 may be integrated with the touchscreen panel 102, or may incorporate therein the functions of the touchscreen panel 102.

The cover glass 103 is a member for protecting the display panel 101 and the touchscreen panel 102, and covers the display panel 101 and the touchscreen panel 102. The cover glass 103 is, for example, a glass substrate. The present invention is not limited to using the cover glass 103. For example, a resin substrate may be provided above the touchscreen panel 102. The surface of the cover glass 103 may be called a detection surface for detecting the finger Fg.

The biological information detection device 1 is provided so as to face the second principal surface 101b of the display panel 101. In other words, the display panel 101 is provided between the biological information detection device 1 and the touchscreen panel 102. The biological information detection device 1 includes a biosensor 10 (refer to FIG. 3) capable of detecting the biological information. Since the biological information detection device 1 and the touchscreen panel 102 are provided so as to overlap each other, the biosensor 10 can be said to be provided to the touchscreen panel 102 that is the input unit.

In the present embodiment, the biosensor 10 is an optical biosensor, and is, for example, a light reflective biological information sensor. The biosensor 10 can detect asperities (for example, a fingerprint) of the surface of the finger Fg or the palm by detecting the light L2 reflected on the interface between the cover glass 103 and air. The biosensor 10 may detect the light L2 reflected in the finger Fg or the palm to detect a vascular pattern, or to detect other biological information. Since the biological information detection device 1 can be easily increased in area, a detection area AA of the biological information detection device 1 is provided so as to face the entire display area DA of the display panel 101. The detection area AA is not limited to this configuration, and may face a portion of the display area DA of the display panel 101. The biological information detection device 1 may be provided between the display panel 101 and the cover glass 103. In this case, the biological information detection device 1 may be provided between the touchscreen panel 102 and the display panel 101, or the biological information detection device 1 may incorporate therein the functions of the touchscreen panel.

Figure 2:
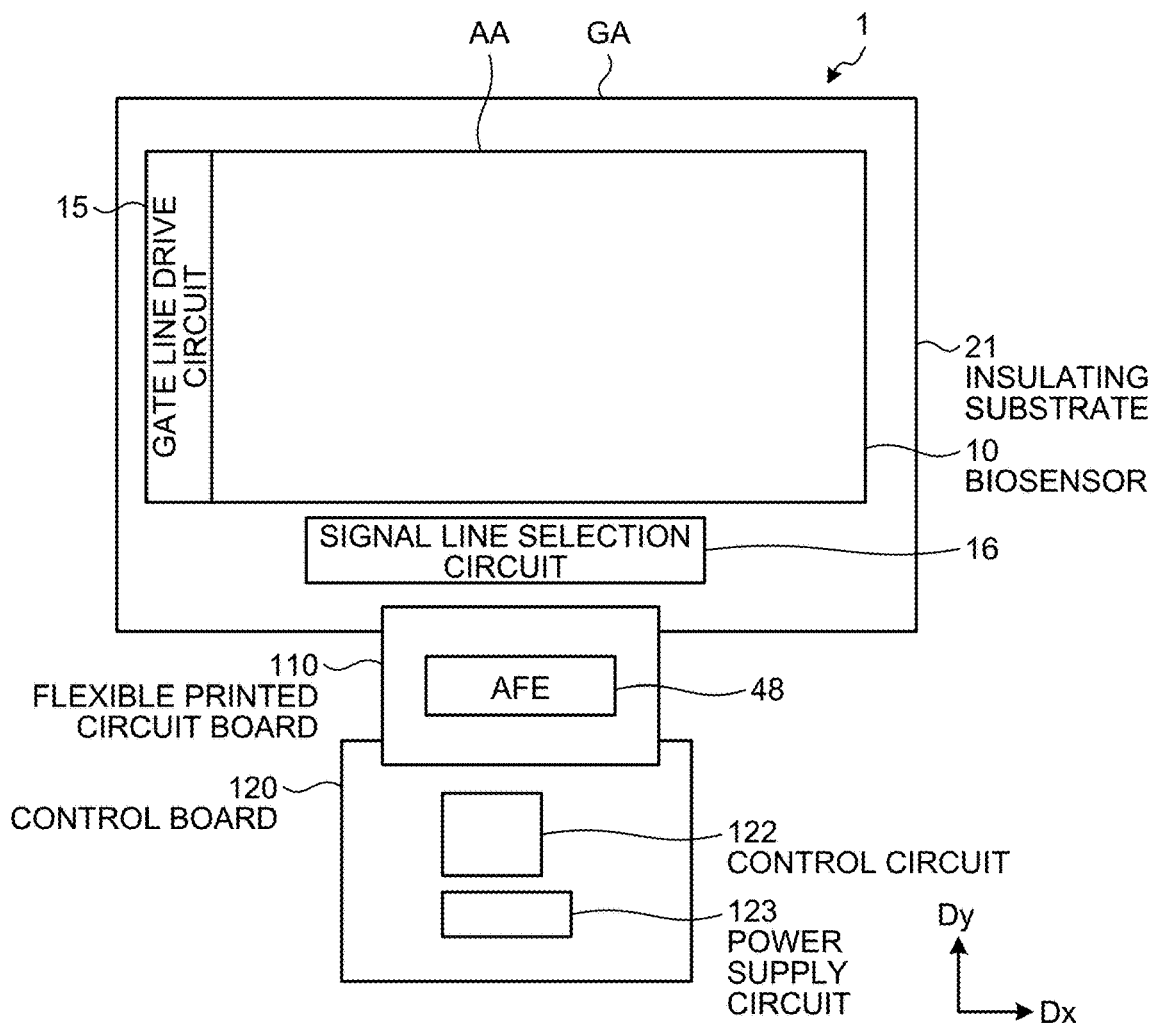
FIG. 2 is a plan view illustrating a biological information detection device according to the embodiment.

FIG. 2 is a plan view illustrating the biological information detection device according to the present embodiment. As illustrated in FIG. 2, the biological information detection device 1 includes an insulating substrate 21, a biosensor 10, a gate line drive circuit 15, a signal line selection circuit 16, an analog front-end circuit (hereinafter, called "AFE") 48, a control circuit 122, and a power supply circuit 123.

As illustrated in FIG. 2, a control board 120 is electrically coupled to the insulating substrate 21 through a flexible printed circuit board 110. The flexible printed circuit board 110 is provided with the AFE 48. The control board 120 is provided with the control circuit 122 and the power supply circuit 123. The control circuit 122 is, for example, a field programmable gate array (FPGA). The control circuit 122 supplies control signals to the biosensor 10, the gate line drive circuit 15, and the signal line selection circuit 16 to control a detection operation of the biosensor 10. The power supply circuit 123 supplies voltage signals including, for example, a power supply signal SVS (refer to FIG. 6) to the biosensor 10 and the gate line drive circuit 15.

The insulating substrate 21 has the detection area AA and a peripheral area GA. The detection area AA is an area overlapping a plurality of first photodiodes PD1 and a plurality of second photodiodes PD2 (refer to FIG. 5) included in the biosensor 10. The peripheral area GA is an area outside the detection area AA, and is an area overlapping neither the first photodiodes PD1 nor the second photodiodes PD2. That is, the peripheral area GA is an area between the outer circumference of the detection area AA and the ends of the insulating substrate 21. The gate line drive circuit 15 and the signal line selection circuit 16 are provided in the peripheral area GA.

Figure 3:
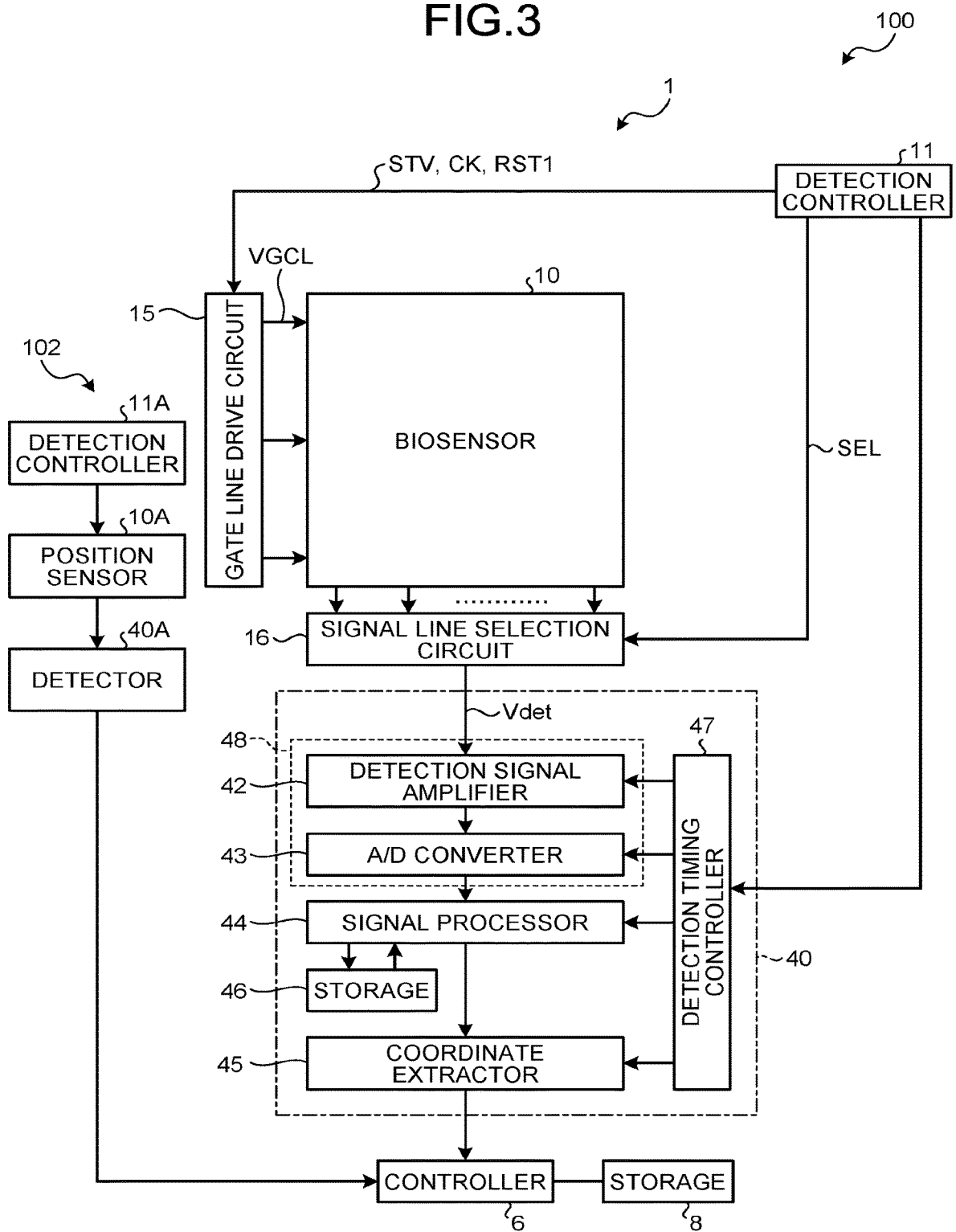
FIG. 3 is a block diagram illustrating a schematic configuration example of the detection device according to the embodiment.

FIG. 3 is a block diagram illustrating a schematic configuration example of the detection device according to the present embodiment. As illustrated in FIG. 3, the biological information detection device 1 further includes a detection controller 11 and a detector 40. The control circuit 122 includes some or all functions of the detection controller 11. The control circuit 122 also includes some or all functions of the detector 40 except the function of the AFE 48.

The biosensor 10 is an optical sensor including the first and the second photodiodes PD1 and PD2 that serve as photoelectric conversion elements. Each of the first and the second photodiodes PD1 and PD2 included in the biosensor 10 outputs an electrical signal corresponding to light emitted thereto as a detection signal Vdet to the signal line selection circuit 16. The biosensor 10 performs the detection in response to a gate drive signal VGCL supplied from the gate line drive circuit 15.

The detection controller 11 is a circuit that supplies respective control signals to the gate line drive circuit 15, the signal line selection circuit 16, and the detector 40 to control operations thereof. The detection controller 11 supplies various control signals including, for example, a start signal STV, a clock signal CK, and a reset signal RST1 to the gate line drive circuit 15. The detection controller 11 also supplies various control signals including, for example, a selection signal SEL to the signal line selection circuit 16.

The gate line drive circuit 15 is a circuit that drives a plurality of gate lines GCL (refer to FIG. 4) based on the various control signals. The gate line drive circuit 15 sequentially or simultaneously selects the gate lines GCL, and supplies the gate drive signals VGCL to the selected gate lines GCL. Through this operation, the gate line drive circuit 15 selects the first and the second photodiodes PD1 and PD2 coupled to the gate lines GCL.

The gate line drive circuit 15 is a circuit that drives a plurality of gate lines GCL (refer to FIG. 4) based on the various control signals. The gate line drive circuit 15 sequentially or simultaneously selects the gate lines GCL, and supplies the gate drive signals VGCL to the selected gate lines GCL. Through this operation, the gate line drive circuit 15 selects the first and the second photodiodes PD1 and PD2 coupled to the gate lines GCL.

Figure 4:
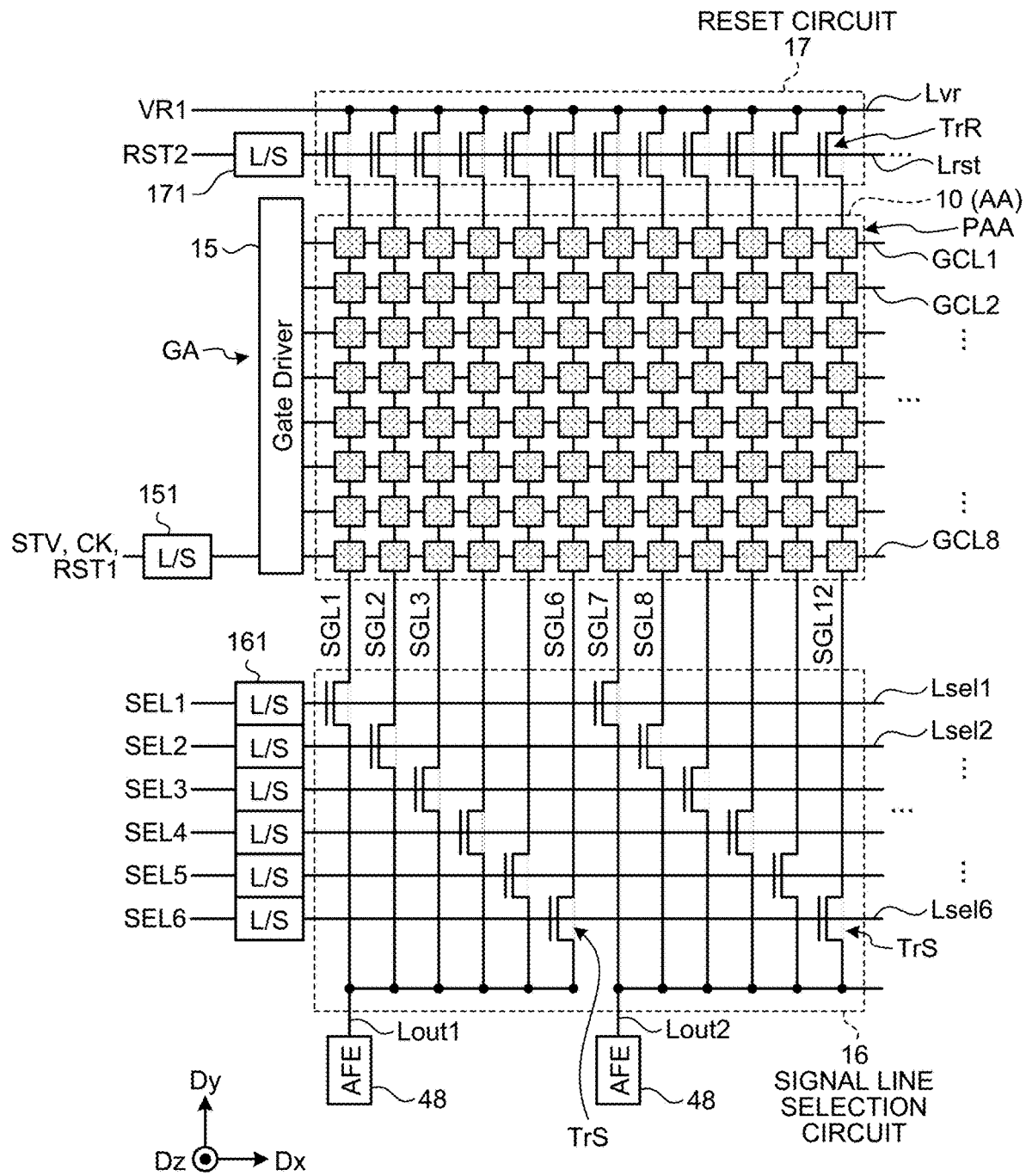
FIG. 4 is a circuit diagram illustrating the biological information detection device.

The signal line selection circuit 16 is a switch circuit that sequentially or simultaneously selects a plurality of signal lines SGL (refer to FIG. 4). The signal line selection circuit 16 couples the selected signal lines SGL to the AFE 48 serving as a detection circuit based on the selection signal SEL supplied from the detection controller 11. Through this operation, the signal line selection circuit 16 outputs the detection signal Vdet of each of the first and the second photodiodes PD1 and PD2 to the detector 40. The signal line selection circuit 16 is, for example, a multiplexer.

The detector 40 is a circuit that includes the AFE 48, a signal processor 44, a coordinate extractor 45, a storage 46, and a detection timing controller 47. The detection timing controller 47 controls, based on a control signal supplied from the detection controller 11, the AFE 48, the signal processor 44, and the coordinate extractor 45 so as to operate in synchronization with one another.

The AFE 48 is a signal processing circuit having functions of at least a detection signal amplifier 42 and an analog-to-digital (A/D) converter 43. The detection signal amplifier 42 amplifies the detection signal Vdet. The A/D converter 43 converts an analog signal output from the detection signal amplifier 42 into a digital signal.

The signal processor 44 is a logic circuit that detects a predetermined physical quantity received by the biosensor 10 based on an output signal of the AFE 48, that is, the digital signal converted from the detection signal Vdet. When the finger Fg or the palm is in proximity to the detection surface, the signal processor 44 can detect the asperities (that is, the fingerprint) of the surface of the finger Fg and the vascular pattern of the finger Fg or the palm based on the detection signal Vdet from the AFE 48.

The storage 46 temporarily stores therein a signal calculated by the signal processor 44. The storage 46 may be, for example, a random-access memory (RAM) or a register circuit.

The coordinate extractor 45 is a logic circuit that obtains the detected coordinates of the asperities of the surface of, for example, the finger Fg when the proximity of the finger Fg or the palm is detected by the signal processor 44. The coordinate extractor 45 combines the detection signals Vdet output from the first and the second photodiodes PD1 and PD2 of the biosensor 10 to generate two-dimensional information representing a shape of the asperities (that is, the fingerprint) of the surface of the finger Fg and a shape of the vascular pattern of the finger Fg or the palm. This two-dimensional information can be said as the biological information on the user. The coordinate extractor 45 may output the detection signals Vdet as sensor outputs Vo, without calculating the detected coordinates. In this case, the detection signals Vdet may be called the biological information on the user.

The touchscreen panel 102 includes the position sensor 10A, a detection controller 11A, and a detector 40A. The detection controller 11A is a circuit that drives the position sensor 10A. The position sensor 10A is driven by the detection controller 11A to output an electronic signal corresponding to the position of the finger Fg or the palm of the user in proximity to the touchscreen panel 102, that is, the operating position, to the detector 40A. The detector 40A may be a circuit having the same configuration as that of the detector 40. The detector 40A extracts information on the operating position based on the electrical signal from the position sensor 10A.

The detection device 100 further includes a controller 6 and a storage 8. The controller 6 is an arithmetic device, that is, a central processing unit (CPU) mounted on the detection device 100. The controller 6 performs various types of processing, for example, by reading a computer program from the storage 8. The storage 8 is a memory for storing therein, for example, content of arithmetic operations in the controller 6 and information on the computer program, and includes at least one of a random-access memory (RAM), a read-only memory (ROM), and an external storage device such as a hard disk drive (HDD). The detection device 100 is incorporated in an electronic apparatus including a display device, for example, a portable electronic apparatus such as a smartphone, a computer, an automated teller machine (ATM), or an entrance management apparatus. All or some of the functions of the storage 8 and the controller 6 can be performed by an arithmetic device and a storage device included in the electronic apparatus.

The controller 6 acquires the information on the operating position from the detector 40A. The controller 6 determines, based on the acquired operating position, whether the user has operated the touchscreen panel 102 along a predetermined trajectory. If the controller 6 determines that the user has operated the touchscreen panel 102 along the predetermined trajectory, the controller 6 acquires the two-dimensional information created by the coordinate extractor 45, that is, the biological information on the user detected by the biosensor 10. The controller 6 reads, from the storage 8, two-dimensional information stored in advance, that is, reference biological information that is the biological information serving as a reference. The controller 6 then checks for a match between the reference biological information and the biological information on the user detected by the biosensor 10 to determine whether the biological information on the user detected by the biosensor 10 matches with the reference biological information. That is, the controller 6 uses the biological information on the user detected by the biosensor 10 to perform user authentication. If the biological information on the user detected by the biosensor 10 matches with the reference biological information, the controller 6 determines that the user has been authenticated, and controls the detection device 100 to execute a predetermined function specified in advance. The predetermined function is, for example, a function required by the user to be performed by the detection device 100, and examples thereof include starting a computer program of the detection device 100, return from a sleep state, and access to a website. If the coordinate extractor 45 does not calculate the detected coordinates, the controller 6 generates the two-dimensional information representing, for example, the shape of the asperities (that is, the fingerprint) of the surface of the finger Fg and the shape of the vascular pattern of the finger Fg or the palm from the detection signal Vdet. A detailed control flow of the controller 6 will be described later.

Overall Configuration of Biological Information Detection Device

Figure 5:
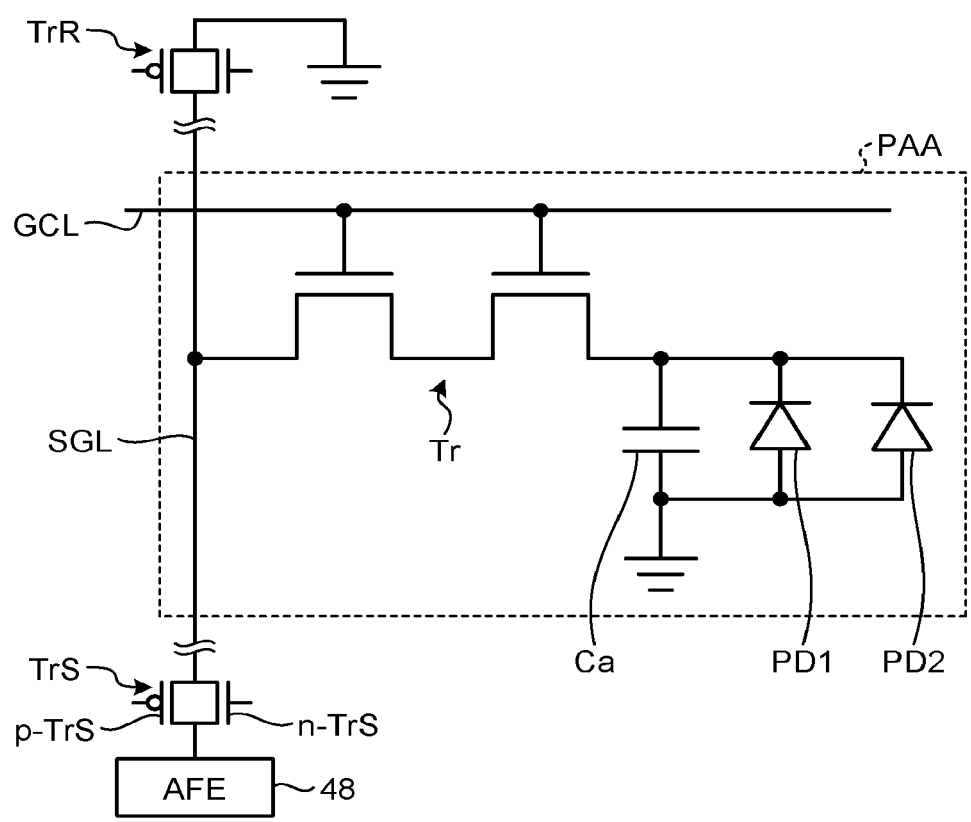
FIG. 5 is an equivalent circuit diagram illustrating a partial detection area.
Figure 6:
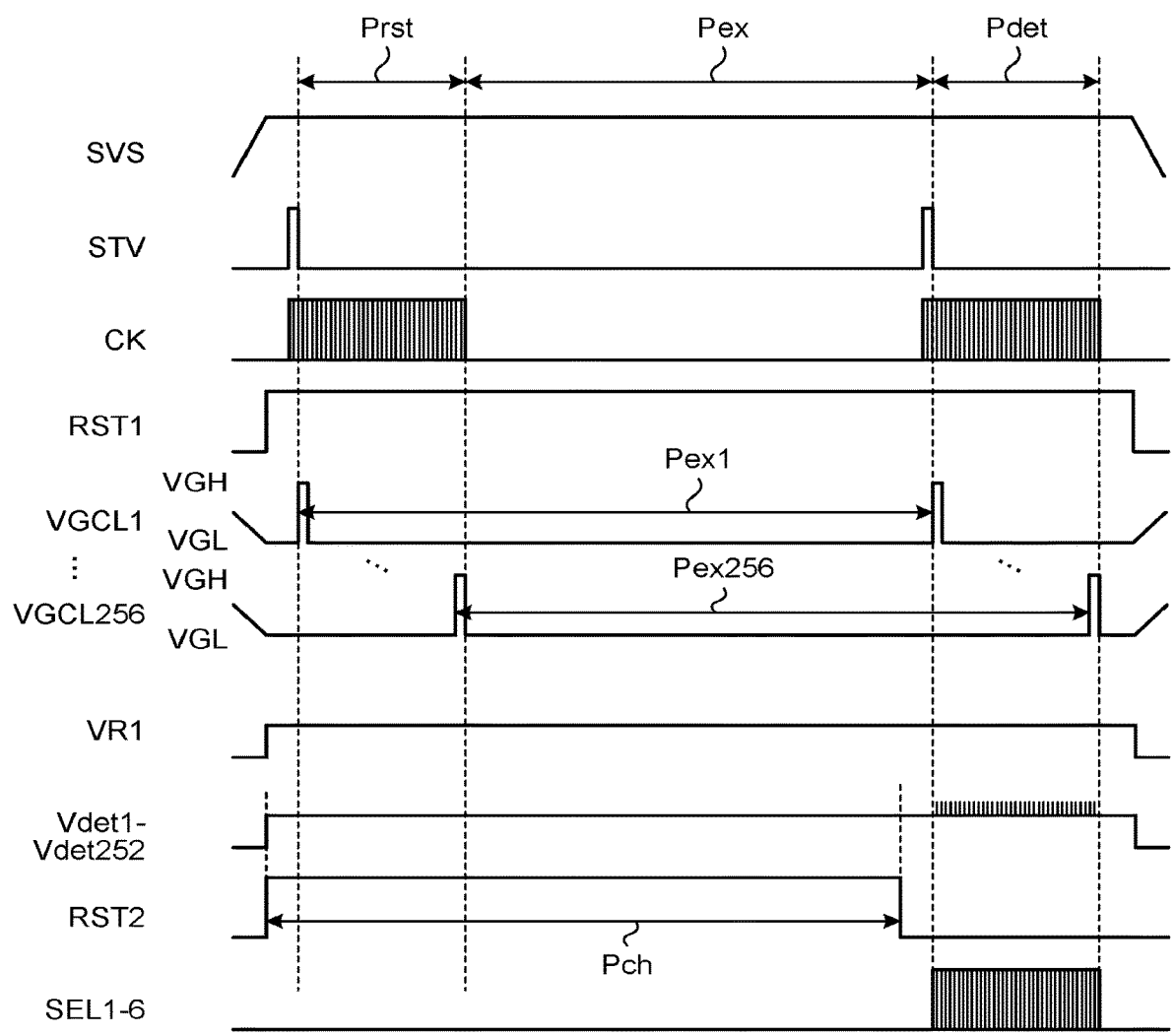
FIG. 6 is a timing waveform diagram illustrating an operation example of the detection device.

The following describes a circuit configuration example and an operation example of the biological information detection device 1. FIG. 4 is a circuit diagram illustrating the biological information detection device. FIG. 5 is an equivalent circuit diagram illustrating a partial detection area. FIG. 6 is a timing waveform diagram illustrating the operation example of the biological information detection device.

As illustrated in FIG. 4, the biosensor 10 has a plurality of partial detection areas PAA arranged in a matrix having a row-column configuration. As illustrated in FIG. 5, each of the partial detection areas PAA includes the first and the second photodiodes PD1 and PD2, a capacitive element Ca, and a first switching element Tr. The first switching element Tr is provided correspondingly to the first and the second photodiodes PD1 and PD2. The first switching element Tr is constituted by a thin-film transistor, and in this example, constituted by an re-channel thin-film transistor (TFT).

The gates of the first switching element Tr are coupled to each of the gate lines GCL. The source of the first switching element Tr is coupled to each of the signal lines SGL. The drain of the first switching element Tr is coupled to a cathode electrode 34 of a corresponding one of the first photodiodes PD1, a cathode electrode 54 of a corresponding one of the second photodiodes PD2, and one end of the capacitive element Ca. An anode electrode 35 of the first photodiode PD1, an anode electrode 55 of the second photodiode PD2, and the other end of the capacitive element Ca are coupled to a reference potential, for example, a ground potential. In this way, the first and the second photodiodes PD1 and PD2 are coupled in parallel in the same direction to the first switching element Tr.

A third switching element TrS and a fourth switching element TrR are coupled to the signal line SGL. The third switching element TrS and the fourth switching element TrR are elements included in a drive circuit that drives the first switching element Tr. In the present embodiment, the drive circuit includes, for example, the gate line drive circuit 15, the signal line selection circuit 16, and a reset circuit 17 that are provided in the peripheral area GA. The third switching element TrS is constituted by, for example, a complementary metal-oxide semiconductor (CMOS) transistor obtained by combining a p-channel transistor p-TrS with an n-channel transistor n-TrS. In the same manner, the fourth switching element TrR is constituted by a CMOS transistor.

When the fourth switching element TrR of the reset circuit 17 is turned on, the capacitive element Ca is supplied with a reference signal VR1 serving as an initial potential of the capacitive element Ca from the power supply circuit 123. This operation resets the capacitive element Ca. When the partial detection area PAA is irradiated with light, a current corresponding to an amount of the light flows through each of the first and the second photodiodes PD1 and PD2. As a result, an electrical charge is stored in the capacitive element Ca. After the first switching element Tr is turned on, a current corresponding to the electrical charge stored in the capacitive element Ca flows through the signal line SGL. The signal line SGL is coupled to the AFE 48 through the third switching element TrS of the signal line selection circuit 16. Thus, the biological information detection device 1 can detect a signal corresponding to the amount of the light emitted to the first and the second photodiodes PD1 and PD2 for each of the partial detection areas PAA.

As illustrated in FIG. 4, the gate lines GCL extend in a first direction Dx, and are coupled to the partial detection areas PAA arranged in the first direction Dx. A plurality of gate lines GCL1, GCL2, . . . , GCL8 are arranged in a second direction Dy, and are each coupled to the gate line drive circuit 15. In the following description, the gate lines GCL1, GCL2, . . . , GCL8 will each be simply referred to as the gate line GCL when need not be distinguished from one another. Although the number of the gate lines GCL is eight, this is merely an example. Eight or more, such as 256, of the gate lines GCL may be arranged.

The first direction Dx is a direction in a plane parallel to the insulating substrate 21, and is, for example, a direction parallel to the gate lines GCL. The second direction Dy is a direction in a plane parallel to the insulating substrate 21, and is, for example, a direction orthogonal to the first direction Dx. The second direction Dy may intersect the first direction Dx without being orthogonal thereto. A third direction Dz is a direction orthogonal to the first direction Dx and the second direction Dy, and is a direction orthogonal to the insulating substrate 21.

The signal lines SGL extend in the second direction Dy, and are coupled to the partial detection areas PAA arranged in the second direction Dy. A plurality of signal lines SGL1, SGL2, . . . , SGL12 are arranged in the first direction Dx, and are each coupled to the signal line selection circuit 16 and the reset circuit 17. Although the number of the signal lines SGL is 12, this is merely an example. Twelve or more, such as 252, of the signal lines SGL may be arranged. In FIG. 4, the biosensor 10 is provided between the signal line selection circuit 16 and the reset circuit 17. The present invention is not limited thereto. The signal line selection circuit 16 and the reset circuit 17 may be coupled to the same ends of the signal lines SGL.

The gate line drive circuit 15 receives the various control signals such as the start signal STV, the clock signal CK, and the reset signal RST1 through a level shifter 151. The gate line drive circuit 15 includes a plurality of second switching elements TrG (not illustrated). The gate line drive circuit 15 sequentially selects the gate lines GCL1, GCL2, . . . , GCL8 in a time-division manner through operations of the second switching elements TrG. The gate line drive circuit 15 supplies the gate drive signal VGCL through a selected one of the gate lines GCL to corresponding ones of the first switching elements Tr. This operation selects the partial detection areas PAA arranged in the first direction Dx as the detection targets.

The signal line selection circuit 16 includes a plurality of selection signal lines Lsel, a plurality of output signal lines Lout, and the third switching elements TrS. The third switching elements TrS are provided correspondingly to the respective signal lines SGL. Six of the signal lines SGL1, SGL2, . . . , SGL6 are coupled to a common output signal line Lout1. Six of the signal lines SGL7, SGL8, . . . , SGL12 are coupled to a common output signal line Lout2. The output signal lines Lout1 and Lout2 are each coupled to the AFE 48.

The signal lines SGL1, SGL2, . . . , SGL6 are grouped into a first signal line block, and the signal lines SGL7, SGL8, . . . , SGL12 are grouped into a second signal line block. The selection signal lines Lsel are coupled to the gates of the respective third switching elements TrS included in one of the signal line blocks. One of the selection signal lines Lsel is coupled to the gates of the third switching elements TrS in the signal line blocks. Specifically, selection signal lines Lsel1, Lsel2, . . . , Lsel6 are coupled to the third switching elements TrS corresponding to the signal lines SGL1, SGL2, . . . , SGL6. The selection signal line Lsel1 is coupled to one of the third switching elements TrS corresponding to the signal line SGL1 and one of the third switching elements TrS corresponding to the signal line SGL7. The selection signal line Lsel2 is coupled to one of the third switching elements TrS corresponding to the signal line SGL2 and one of the third switching elements TrS corresponding to the signal line SGL8.

The control circuit 122 (refer to FIG. 2) sequentially supplies the selection signals SEL to the selection signal lines Lsel through level shifters 161. This operation causes the signal line selection circuit 16 to operate the third switching elements TrS to sequentially select the signal lines SGL in one of the signal line blocks in a time-division manner. The signal line selection circuit 16 simultaneously selects one of the signal lines SGL in each of the signal line blocks. With the above-described configuration, the biological information detection device 1 can reduce the number of integrated circuits (ICs) including the AFE 48 or the number of terminals of the ICs.

As illustrated in FIG. 4, the reset circuit 17 includes a reference signal line Lvr, a reset signal line Lrst, and the fourth switching elements TrR. The fourth switching elements TrR are provided correspondingly to the signal lines SGL. The reference signal line Lvr is coupled to either the sources or the drains of the fourth switching elements TrR. The reset signal line Lrst is coupled to the gates of the fourth switching elements TrR.

The control circuit 122 supplies a reset signal RST2 to the reset signal line Lrst through a level shifter 171. This operation turns on the fourth switching elements TrR to electrically couple the signal lines SGL to the reference signal line Lvr. The power supply circuit 123 supplies the reference signal VR1 to the reference signal line Lvr. This operation supplies the reference signal VR1 to the capacitive elements Ca included in the partial detection areas PAA.

As illustrated in FIG. 6, the biological information detection device 1 includes a reset period Prst, an exposure period Pex, and a reading period Pdet. The power supply circuit 123 supplies the power supply signal SVS to the first and the second photodiodes PD1 and PD2 through the reset period Prst, the exposure period Pex, and the reading period Pdet. The control circuit 122 supplies the reference signal VR1 and the reset signal RST2 serving as high-level voltage signals to the reset circuit 17 from a time before the reset period Prst starts. The control circuit 122 supplies the start signal STV to the gate line drive circuit 15, and the reset period Prst starts.

During the reset period Prst, the gate line drive circuit 15 sequentially selects the gate line GCL based on the start signal STV, the clock signal CK, and the reset signal RST1. The gate line drive circuit 15 sequentially supplies the gate drive signal VGCL to the gate line GCL. The gate drive signal VGCL has a pulsed waveform having a high-level voltage VGH and a low-level voltage VGL. In FIG. 6, 256 of the gate lines GCL are provided, and gate drive signals VGCL1, . . . , VGCL256 are sequentially supplied to the gate lines GCL.

Thus, during the reset period Prst, the capacitive elements Ca of all the partial detection areas PAA are sequentially electrically coupled to the signal lines SGL, and are supplied with the reference signal VR1. As a result, capacities of the capacitive elements Ca are reset.

After the gate drive signal VGCL256 is supplied to the gate line GCL, the exposure period Pex starts. The start timing and end timing of actual exposure periods Pex1, . . . , Pex256 in the partial detection areas PAA corresponding to the respective gate lines GCL differ from one another. Each of the exposure periods Pex1, . . . , Pex256 starts at a time when the gate drive signal VGCL changes from the high-level voltage VGH to the low-level voltage VGL during the reset period Prst. Each of the exposure periods Pex1, . . . , Pex256 ends at a time when the gate drive signal VGCL changes from the low-level voltage VGL to the high-level voltage VGH during the reading period Pdet. The lengths of exposure time of the exposure periods Pex1, . . . , Pex256 are equal.

During the exposure period Pex, the current corresponding to the light emitted to the first and the second photodiodes PD1 and PD2 flows in each of the partial detection areas PAA. As a result, the electrical charge is stored in each of the capacitive elements Ca.

At a time before the reading period Pdet starts, the control circuit 122 sets the reset signal RST2 to a low-level voltage. This operation stops the reset circuit 17 operating. During the reading period Pdet, the gate line drive circuit 15 sequentially supplies the gate drive signals VGCL1, . . . , VGCL256 to the gate lines GCL in the same manner as during the reset period Prst.

For example, during a period in which the gate drive signal VGCL1 is at the high-level voltage VGH, the control circuit 122 sequentially supplies selection signals SEL1, . . . , SEL6 to the signal line selection circuit 16. This operation sequentially or simultaneously couples the signal lines SGL for the partial detection areas PAA selected by the gate drive signal VGCL1 to the AFE 48. As a result, the detection signal Vdet is supplied to the AFE 48. In the same manner, the signal line selection circuit 16 sequentially selects the signal line SGL in each period in which a corresponding one of the gate drive signals VGCL is set to the high-level voltage VGH. Thus, the biological information detection device 1 can output the detection signals Vdet of all the partial detection areas PAA to the AFE 48 during the reading period Pdet.

The biological information detection device 1 may perform the detection by repeatedly performing the processing during the reset period Prst, the exposure period Pex, and the reading period Pdet. Alternatively, the biological information detection device 1 may start the detection operation when having detected that the finger Fg, for example, is in contact with or in proximity to the detection surface.

Figure 7:
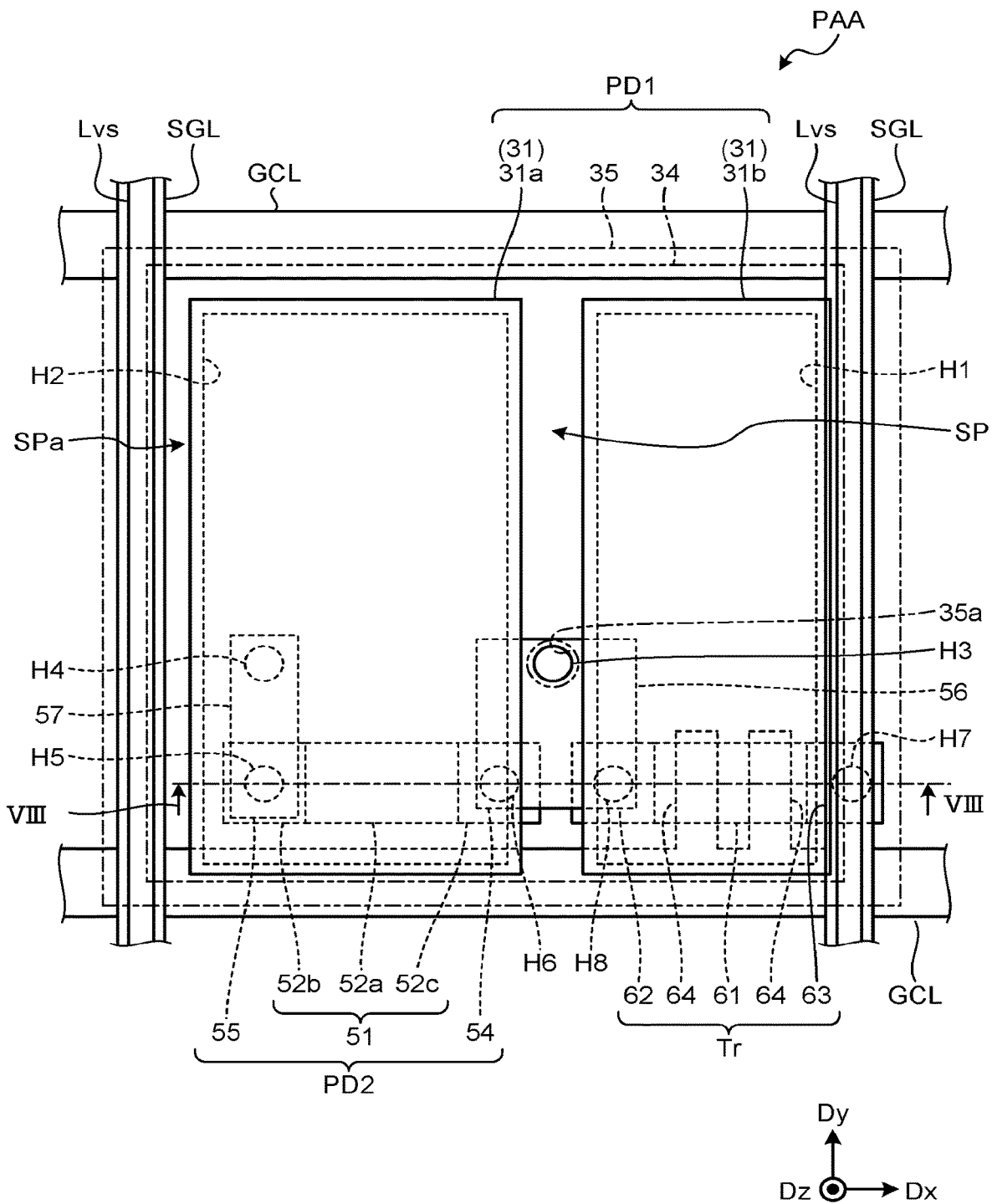
FIG. 7 is a plan view schematically illustrating the partial detection area of the biological information detection device.
Figure 8:
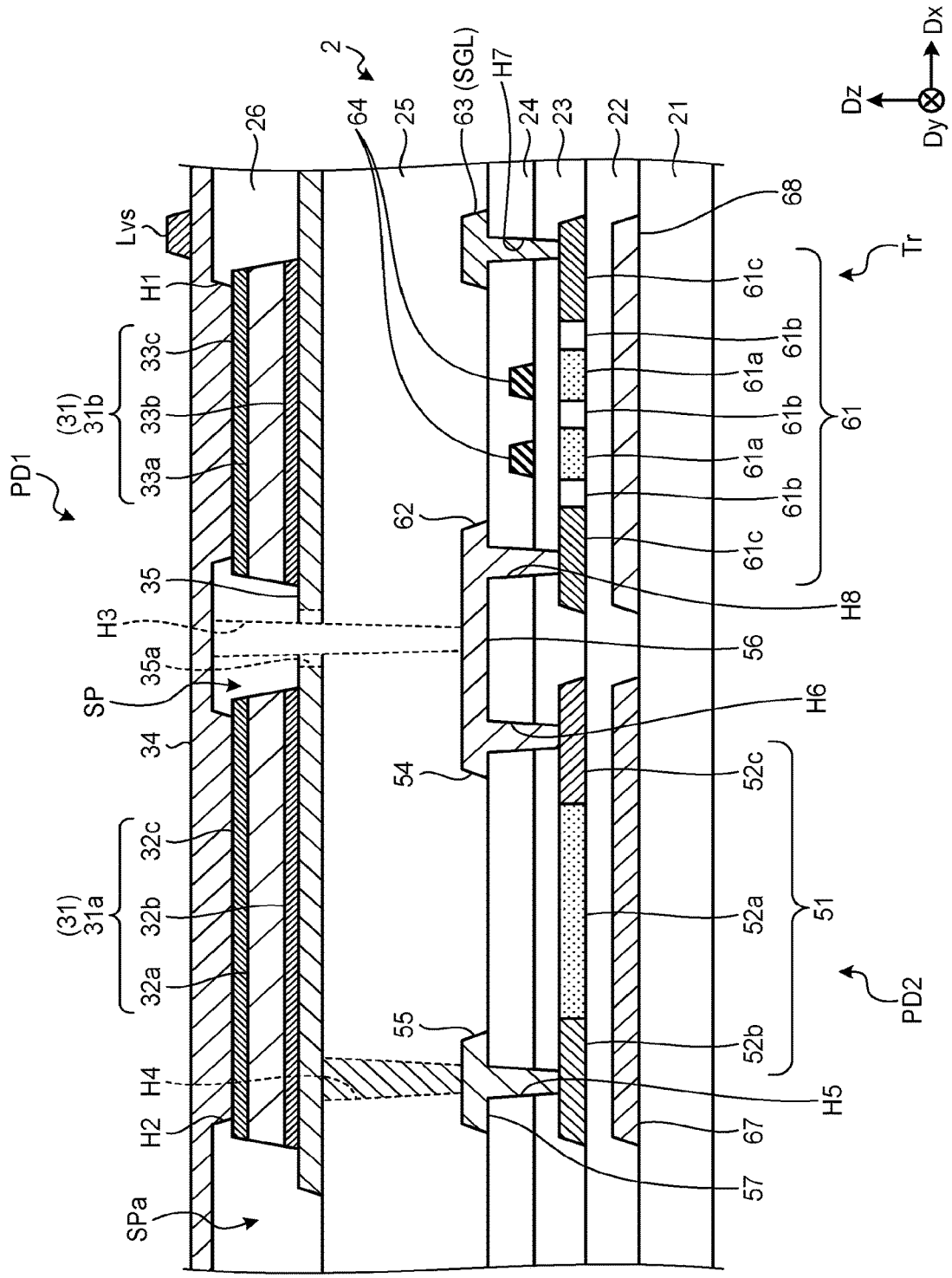
FIG. 8 is a VIII-VIII' sectional view of FIG. 7.

The following describes a detailed configuration of the biological information detection device 1. FIG. 7 is a plan view schematically illustrating the partial detection area of the biological information detection device. FIG. 8 is a VIII-VIII' sectional view of FIG. 7. For ease of viewing, FIG. 7 illustrates the cathode electrode 34 and the anode electrode 35 with long dashed double-short dashed lines.

In the following description, in a direction orthogonal to a surface of the insulating substrate 21, a direction from the insulating substrate 21 toward the first photodiode PD1 will be referred to as the "upper side" or simply as "above", and a direction from the first photodiode PD1 toward the insulating substrate 21 will be referred to as the "lower side" or simply as "below". The term "plan view" refers to a case of viewing from the direction orthogonal to the surface of the insulating substrate 21.

As illustrated in FIG. 7, the partial detection area PAA is an area surrounded by the gate lines GCL and the signal lines SGL. The first photodiode PD1, the second photodiode PD2, and the first switching element Tr are provided in the partial detection area PAA, that is, in the area surrounded by the gate lines GCL and the signal lines SGL. Each of the first and the second photodiodes PD1 and PD2 is, for example, a positive-intrinsic-negative (PIN) photodiode.

The first photodiode PD1 includes a first semiconductor layer 31, the cathode electrode 34 and the anode electrode 35. The first semiconductor layer 31 includes a first partial semiconductor layer 31a and a second partial semiconductor layer 31b. The first and the second partial semiconductor layers 31a and 31b of the first photodiode PD1 are of amorphous silicon (a-Si). The first and the second partial semiconductor layers 31a and 31b are provided adjacent to each other with a space SP provided therebetween in the first direction Dx. The cathode electrode 34 and the anode electrode 35 are continuously provided over an area overlapping the first partial semiconductor layer 31a, the second partial semiconductor layer 31b, and the space SP. In the following description, the first and the second partial semiconductor layers 31a and 31b may each be simply referred to as the first semiconductor layer 31 when need not be distinguished from one another.

The first photodiode PD1 is provided so as to overlap the second photodiode PD2. Specifically, the first partial semiconductor layer 31a of the first photodiode PD1 overlaps the second photodiode PD2. The second photodiode PD2 includes a second semiconductor layer 51, the cathode electrode 54, and the anode electrode 55. The second semiconductor layer 51 is of polysilicon. The second semiconductor layer 51 is more preferably of low-temperature polysilicon (hereinafter, referred to as low-temperature polycrystalline silicon (LTPS)).

The second semiconductor layer 51 has an i region 52a, a p region 52b, and an n region 52c. The i region 52a is disposed between the p region 52b and the n region 52c in plan view. Specifically, the p region 52b, the i region 52a, and the n region 52c are arranged in this order in the first direction Dx. The polysilicon of the n region 52c is doped with impurities to form an n+ region. The polysilicon of the p region 52b is doped with impurities to form a p+ region. The i region 52a is, for example, a non-doped intrinsic semiconductor, and has lower conductivity than those of the p region 52b and the n region 52c.

The second semiconductor layer 51 is coupled to the first partial semiconductor layer 31a of the first photodiode PD1 through a first relay electrode 56 and a second relay electrode 57. In the present embodiment, a portion of the first relay electrode 56 overlapping the second semiconductor layer 51 serves as the cathode electrode 54, and a portion of the second relay electrode 57 overlapping the second semiconductor layer 51 serves as the anode electrode 55. A detailed coupling configuration between the second semiconductor layer 51 and the first photodiode PD1 will be described later.

The first switching element Tr is provided in an area overlapping the second partial semiconductor layer 31b of the first photodiode PD1. The first switching element Tr includes a third semiconductor layer 61, a source electrode 62, a drain electrode 63, and gate electrodes 64. The third semiconductor layer 61 is of polysilicon in the same manner as the second semiconductor layer 51. The third semiconductor layer 61 is more preferably of LTPS.

In the present embodiment, a portion of the first relay electrode 56 overlapping the third semiconductor layer 61 serves as the source electrode 62, and a portion of the signal line SGL overlapping the third semiconductor layer 61 serves as the drain electrode 63. The gate electrodes 64 branch in the second direction Dy from the gate line GCL, and overlap the third semiconductor layer 61. In the present embodiment, the two gate electrodes 64 are provided so as to overlap the third semiconductor layer 61 to form what is called a double-gate structure.

The first switching element Tr is coupled to the cathode electrode 34 of the first photodiode PD1 and the cathode electrode 54 of the second photodiode PD2 through the first relay electrode 56. The first switching element Tr is also coupled to the signal line SGL.

More specifically, the first switching element Tr is provided on the insulating substrate 21 as illustrated in FIG. 8. The insulating substrate 21 is, for example, a light-transmitting glass substrate. The insulating substrate 21 may alternatively be a resin substrate or a resin film formed of a light-transmitting resin such as polyimide. In the biological information detection device 1, the first photodiode PD1, the second photodiode PD2, and the first switching element Tr are formed above the insulating substrate 21. This configuration allows the biological information detection device 1 to have an area of the detection area AA larger than that in a case of using a semiconductor substrate such as a silicon substrate.

Light-blocking layers 67 and 68 are provided above the insulating substrate 21. An undercoat film 22 is provided above the insulating substrate 21 so as to cover the light-blocking layers 67 and 68. The undercoat film 22, a gate insulating film 23, and a first interlayer insulating film 24 are inorganic insulating films, and are formed using, for example, a silicon oxide (SiO) film, a silicon nitride (SiN)

film, or a silicon oxynitride (SiON) film. Each of the inorganic insulating films is not limited to a single layer, but may be a laminated film.

The second semiconductor layer 51 and the third semiconductor layer 61 are provided above the undercoat film 22. That is, the second semiconductor layer 51 of the second photodiode PD2 and the third semiconductor layer 61 of the first switching element Tr are provided in the same layer. The light-blocking layer 67 is provided between the second semiconductor layer 51 and the insulating substrate 21 in the third direction Dz. This configuration can restrain the light L1 from directly irradiating the second photodiode PD2. The light-blocking layer 68 is provided between the third semiconductor layer 61 and the insulating substrate 21 in the third direction Dz. This configuration can reduce a light leakage current of the first switching element Tr.

The third semiconductor layer 61 includes i regions 61a, lightly doped drain (LDD) regions 61b, and n regions 61c. The i regions 61a are formed in areas overlapping the respective gate electrodes 64. The n regions 61c are high-concentration impurity regions that are formed in areas coupled to the source electrode 62 and the drain electrode 63. The LDD regions 61b are low-concentration impurity regions that are formed between the n regions 61c and the i regions 61a and between the two i regions 61a.

The gate insulating film 23 is provided above the undercoat film 22 so as to cover the second semiconductor layer 51 and the third semiconductor layer 61. The gate electrodes 64 are provided above the gate insulating film 23. That is, the first switching element Tr has what is called a top-gate structure in which the gate electrodes 64 are provided on the upper side of the third semiconductor layer 61. However, the first switching element Tr may have what is called a dual-gate structure in which the gate electrodes 64 are provided on both the upper side and the lower side of the third semiconductor layer 61, or may have a bottom-gate structure in which the gate electrodes 64 are provided on the lower side of the third semiconductor layer 61.

The first interlayer insulating film 24 is provided above the gate insulating film 23 so as to cover the gate electrodes 64. The first interlayer insulating film 24 is also provided on the upper side of the second semiconductor layer 51. The first relay electrode 56, the second relay electrode 57, and the signal line SGL are provided above the first interlayer insulating film 24. In the first switching element Tr, the source electrode 62 (first relay electrode 56) is coupled to the third semiconductor layer 61 through a contact hole H8, and the drain electrode 63 (signal line SGL) is coupled to the third semiconductor layer 61 through a contact hole H7.

In the second photodiode PD2, the cathode electrode 54 (first relay electrode 56) is coupled to the n region 52c of the second semiconductor layer 51 through a contact hole H6. This configuration couples the cathode electrode 54 of the second photodiode PD2 to the first switching element Tr. The anode electrode 55 (second relay electrode 57) is coupled to the p region 52b of the second semiconductor layer 51 through a contact hole H5.

A second interlayer insulating film 25 is provided above the first interlayer insulating film 24 so as to cover the second photodiode PD2 and the first switching element Tr. The second interlayer insulating film 25 is an organic film, and is a planarizing film that planarizes asperities formed by various conductive layers. The second interlayer insulating film 25 may be formed of one of the above-mentioned inorganic materials.

The anode electrode 35 of the first photodiode PD1 is provided above the second interlayer insulating film 25 of a backplane 2. The anode electrode 35, the first and the second partial semiconductor layers 31a and 31b, and the cathode electrode 34 are stacked in this order to form the first photodiode PD1. The backplane 2 is a drive circuit board that drives the sensor on a per predetermined detection area basis. The backplane 2 includes the insulating substrate 21, and the first switching elements Tr, the second switching elements TrG, various types of wiring, and so forth provided on the insulating substrate 21.

The first partial semiconductor layer 31a includes an i-type semiconductor layer 32a, a p-type semiconductor layer 32b, and an n-type semiconductor layer 32c. The second partial semiconductor layer 31b includes an i-type semiconductor layer 33a, a p-type semiconductor layer 33b, and an n-type semiconductor layer 33c. The i-type semiconductor layers 32a, 33a, the p-type semiconductor layers 32b, 33b, and the n-type semiconductor layers 32c, 33c are specific examples of the photoelectric conversion elements. In FIG. 8, the i-type semiconductor layers 32a, 33a are provided between the p-type semiconductor layers 32b, 33b and the n-type semiconductor layers 32c, 33c in the direction (third direction Dz) orthogonal to the surface of the insulating substrate 21. In the present embodiment, the p-type semiconductor layers 32b, 33b, the i-type semiconductor layers 32a, 33a, and the n-type semiconductor layers 32c, 33c are stacked in this order above the anode electrode 35.

In the n-type semiconductor layers 32c, 33c, a-Si is doped with impurities to form the n+ regions. In the p-type semiconductor layers 32b, 33b, a-Si is doped with impurities to form the p+ regions. The i-type semiconductor layers 32a, 33a are, for example, non-doped intrinsic semiconductors, and have lower conductivity than those of the n-type semiconductor layers 32c, 33c and the p-type semiconductor layers 32b, 33b.

The cathode electrode 34 and the anode electrode 35 are of a light-transmitting conductive material such as indium tin oxide (ITO). The cathode electrode 34 is an electrode for supplying the power supply signal SVS to the photoelectric conversion layer. The anode electrode 35 is an electrode for reading the detection signal Vdet.

The anode electrode 35 is provided above the second interlayer insulating film 25. The anode electrode 35 is continuously provided across the first and the second partial semiconductor layers 31a and 31b. The anode electrode 35 is coupled to the second relay electrode 57 through a contact hole H4 provided in the second interlayer insulating film 25.

A third interlayer insulating film 26 is provided so as to cover the first and the second partial semiconductor layers 31a and 31b. The third interlayer insulating film 26 is an organic film, and is a planarizing film that planarizes asperities formed by the first and the second partial semiconductor layers 31a and 31b. The cathode electrode 34 is provided above the third interlayer insulating film 26. The cathode electrode 34 is continuously provided above the first and the second partial semiconductor layers 31a and 31b. The cathode electrode 34 is coupled to the first and the second partial semiconductor layers 31a and 31b through contact holes H2 and H1 provided in the third interlayer insulating film 26. With this configuration, the first and the second partial semiconductor layers 31a and 31b are coupled in parallel between the anode electrode 35 and the cathode electrode 34, and serve as one photoelectric conversion element.

The cathode electrode 34 is coupled to the first relay electrode 56 through a contact hole H3 in the space SP between the first and the second partial semiconductor layers 31a and 31b. The contact hole H3 is a through-hole passing through the second interlayer insulating film 25 and the third interlayer insulating film 26 in the third direction Dz. An opening 35a is provided at a portion of the anode electrode 35 overlapping the contact hole H3, and the contact hole H3 is formed through the opening 35a. With the above-described configuration, the cathode electrode 34 of the first photodiode PD1 and the cathode electrode 54 of the second photodiode PD2 are coupled to the first switching element Tr through the first relay electrode 56. In addition, the anode electrode 35 of the first photodiode PD1 is couple to the anode electrode 55 of the second photodiode PD2 through the second relay electrode 57.

The capacity of the capacitive element Ca illustrated in FIG. 5 is provided in the space SP located between the anode electrode 55 and the cathode electrode 34 facing each other with the third interlayer insulating film 26 interposed therebetween, or is provided in a space SPa at the periphery of the first photodiode PD1 located between the anode electrode 55 and the cathode electrode 34 facing each other with the third interlayer insulating film 26 interposed therebetween. The capacitive element Ca stores therein a positive electrical charge during the exposure period Pex.

Figure 9:
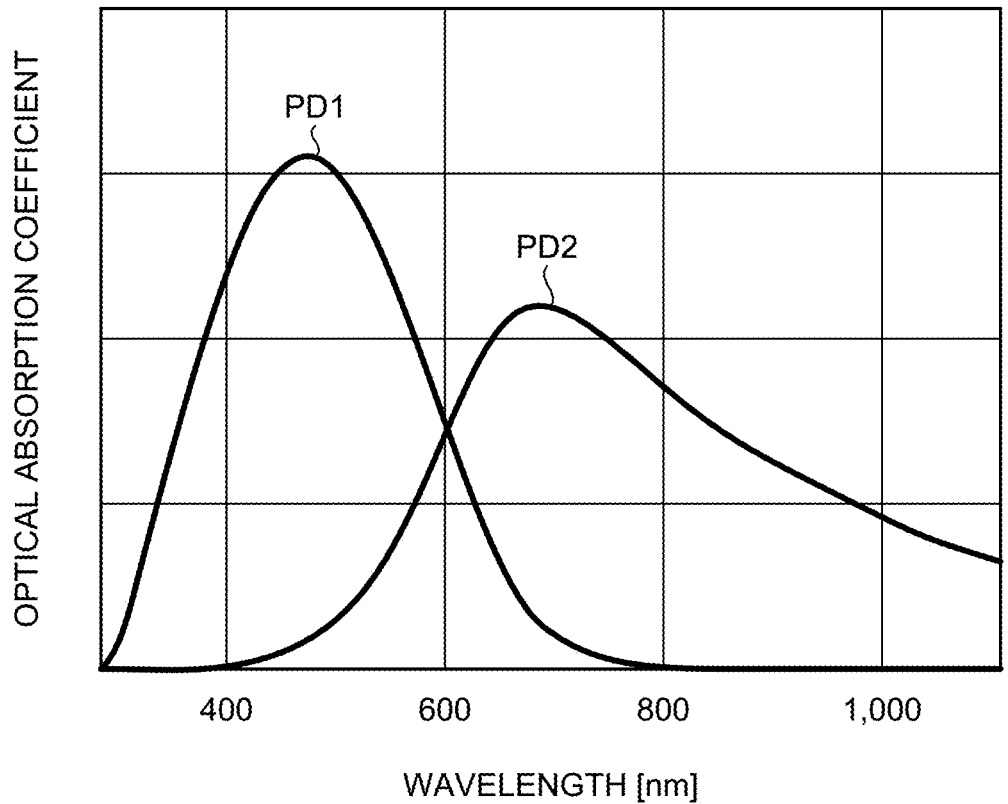
FIG. 9 is a graph schematically illustrating a relation between a wavelength and an optical absorption coefficient of each of a first photodiode and a second photodiode.

FIG. 9 is a graph schematically illustrating a relation between a wavelength and an optical absorption coefficient of each of the first photodiode and the second photodiode. In FIG. 9, the horizontal axis represents the wavelength, and the vertical axis represents the optical absorption coefficient. The optical absorption coefficient is an optical constant that represents a degree of absorption of light traveling through a substance.

As illustrated in FIG. 9, the first photodiode PD1 containing a-Si exhibits a good optical absorption coefficient in the visible light range, for example, in a wavelength range from 300 nm to 800 nm. In contrast, the second photodiode PD2 containing polysilicon exhibits a good optical absorption coefficient in a range of, for example, from 500 nm to 1100 nm, including visible to infrared ranges. In other words, the first photodiode PD1 has high sensitivity in the visible light range, and the second photodiode PD2 has high sensitivity in a range from the red wavelength range to the infrared range that differs from the range of the first photodiode PD1.

In the biological information detection device 1 of the present embodiment, the first and the second photodiodes PD1 and PD2 having different sensitive wavelength ranges are stacked. With this configuration, the wavelength range having high sensitivity can be wider than in a configuration including only either of the photodiodes.

The light L1 (refer to FIG. 1) penetrates the biological information detection device 1 through the space SP and the space SPa. The light L2 reflected by the finger Fg (refer to FIG. 1) enters the first photodiode PD1. Of the light L2, light in a wavelength range not absorbed by the first photodiode PD1 passes through the first photodiode PD1, and enters the second photodiode PD2. For example, in the fingerprint detection, the first photodiode PD1 can well detect the blue or green light L2. In the vascular pattern (for example, vein pattern) detection, the infrared light L2 is not absorbed by the first photodiode PD1, and enters the second photodiode PD2. Thus, the second photodiode PD2 can well detect the infrared light L2. As a result, the biological information detection device 1 can detect the various types of biological information using the same device (biological information detection device 1).

Even if the i region 52a of the second photodiode PD2 has changed to the n-type under the influence of electrical charges or impurities of the insulating films including, for example, the first interlayer insulating film 24, the i region 52a is neutralized by the cathode electrode 34 of the first photodiode PD1. As a result, the biological information detection device 1 can be increased in optical sensitivity.

The first and the second photodiodes PD1 and PD2 are provided in the partial detection area PAA, that is, in the area surrounded by the gate lines GCL and the signal lines SGL. With this configuration, the number of switching elements and the number of wires can be smaller than in a case where each of the first and the second photodiodes PD1 and PD2 is provided with the first switching element Tr, the gate line GCL, and the signal line SGL. Accordingly, the biological information detection device 1 can improve the resolution of the detection.

As described above, the biosensor 10 includes the first photodiode PD1 including the first semiconductor layer 31 containing amorphous silicon and the second photodiode PD2 including the second semiconductor layer 51 containing polysilicon. In the biosensor 10, the first semiconductor layer 31 containing amorphous silicon and the second semiconductor layer 51 containing polysilicon, that is, the first and the second photodiodes PD1 and PD2 are stacked so as to overlap each other in the third direction Dz. However, in the biosensor 10, the first and the second photodiodes PD1 and PD2 need not be stacked in the third direction Dz, and may be provided, for example, in the same layer.

The biosensor 10 can detect, as the biological information, the fingerprint of the user using the first photodiode PD1, and the vascular pattern of the user using the second photodiode PD2. The vascular pattern refers to an image of blood vessels, and is the vein pattern in the present embodiment. Although the biosensor 10 detects the fingerprint and the vascular pattern as the biological information on the user, the biosensor 10 may detect at least one of the fingerprint and the vascular pattern. The biosensor 10 may detect the biological information (for example, pulsation and/or a pulse wave) other than the fingerprint and the vascular pattern.

Figure 10:
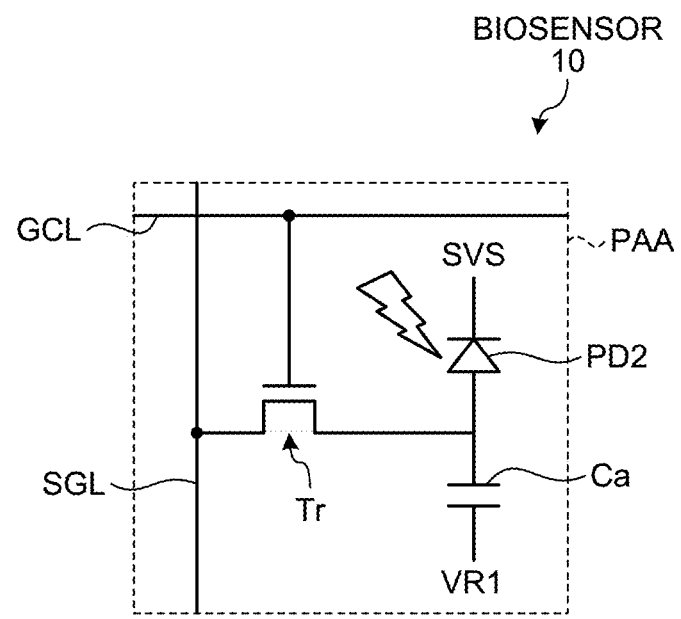
FIG. 10 is an equivalent circuit diagram illustrating the partial detection area according to another example.

An exemplary case will be described where the biosensor 10 detects only one of the fingerprint and the vascular pattern. The following describes an exemplary case where the biosensor 10 detects the vascular pattern without detecting the fingerprint. FIG. 10 is an equivalent circuit diagram illustrating the partial detection area according to another example. As illustrated in FIG. 10, the biosensor 10 in this example has the partial detection areas PAA arranged in a matrix having a row-column configuration. As illustrated in FIG. 10, the partial detection areas PAA of the biosensor 10 includes the second photodiode PD2, the capacitive element Ca, and the first switching element Tr. The first switching element Tr is provided correspondingly to the second photodiode PD2. The gate of the first switching element Tr is coupled to the gate line GCL. The source of the first switching element Tr is coupled to the signal line SGL. The drain of the first switching element Tr is coupled to the cathode electrode 54 of the second photodiode PD2 and one end of the capacitive element Ca. The anode electrode 55 of the second photodiode PD2 and the other end of the capacitive element Ca are coupled to the reference potential, for example, the ground potential. That is, the biosensor 10 has a configuration not including the first photodiode PD1.

Figure 11:
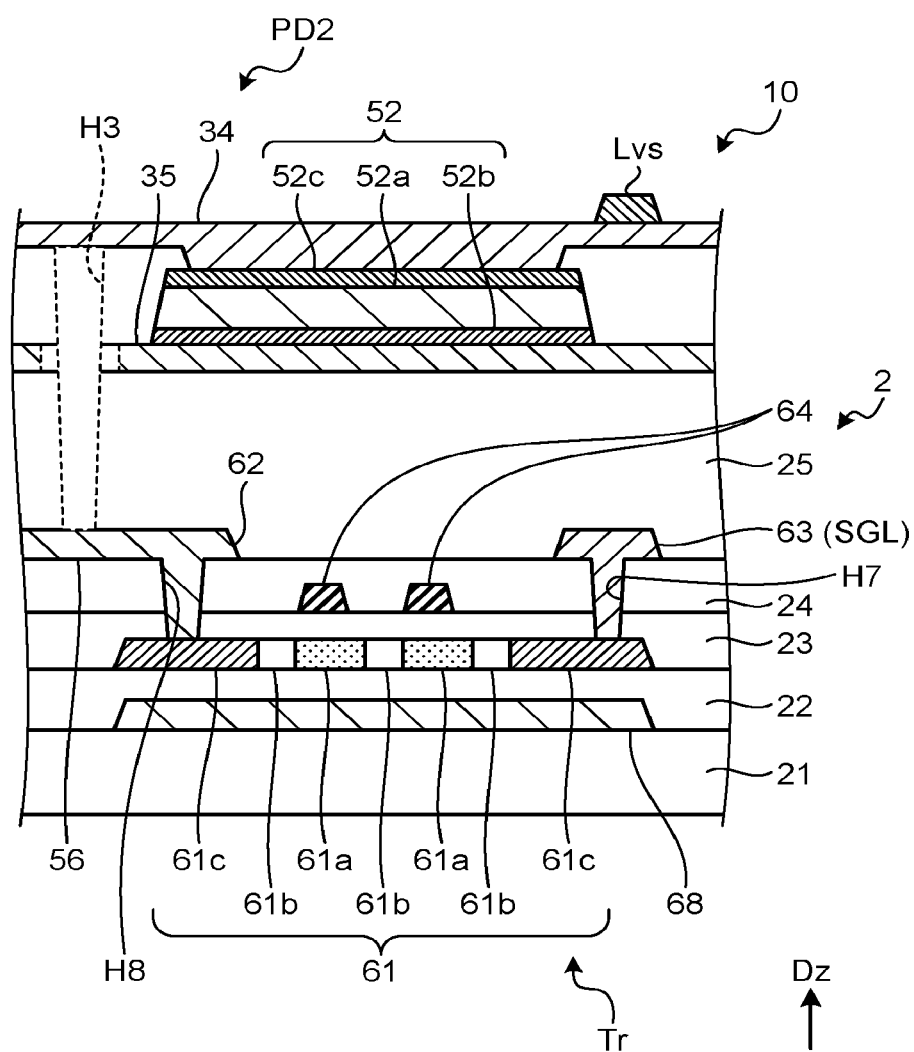
FIG. 11 is a schematic sectional view of the partial detection area according to the other example.

FIG. 11 is a schematic sectional view of the partial detection area according to the other example. As illustrated in FIG. 11, the biosensor 10 in this example is provided with the first switching element Tr above the insulating substrate 21 in the same manner as in FIG. 8.

However, unlike in FIG. 8, the biosensor 10 in this example is not provided with the first photodiode PD1. In addition, the biosensor 10 in this example is provided with the second photodiode PD2 at a location different from that in FIG. 8. In the biosensor 10 of this example, the second photodiode PD2 is provided on the upper side, that is, in the third direction Dz of the first switching element Tr. That is, the anode electrode 35 of the second photodiode PD2 is provided above the second interlayer insulating film 25. The second photodiode PD2 is stacked in the order of the anode electrode 35, the second semiconductor layer 51, and the cathode electrode 34. The second semiconductor layer 51 is stacked in the order of the p region 52b, the i region 52a, and the n region 52c above the anode electrode 35. The anode electrode 35 is coupled to the source electrode 62 of the first switching element Tr through the contact hole H4 provided in the second interlayer insulating film 25.

As described above, the biosensor 10 includes the second photodiode PD2 including the second semiconductor layer 51 containing polysilicon, and need not include the first photodiode PD1. In this case, the biosensor 10 includes the second photodiode PD2, and thus, can suitably detect the vascular pattern of the user.

When the biosensor 10 is a sensor that detects the fingerprint of the user and does not detect the vascular pattern of the user, the biosensor 10 has a configuration including the first photodiode PD1 without including the second photodiode PD2. In that case, the equivalent circuit of the biosensor 10 is preferably obtained by replacing the second photodiode PD2 in FIG. 10 with the first photodiode PD1, and the stacking configuration of the biosensor 10 is preferably obtained by replacing the second photodiode PD2 in FIG. 11 with the first photodiode PD1. While the stacking configuration of the biosensor 10 has been described above, the structure of the biosensor 10 is not limited to that described above, and may be any structure as long as being capable of detecting the biological information on the user.

Figure 12:
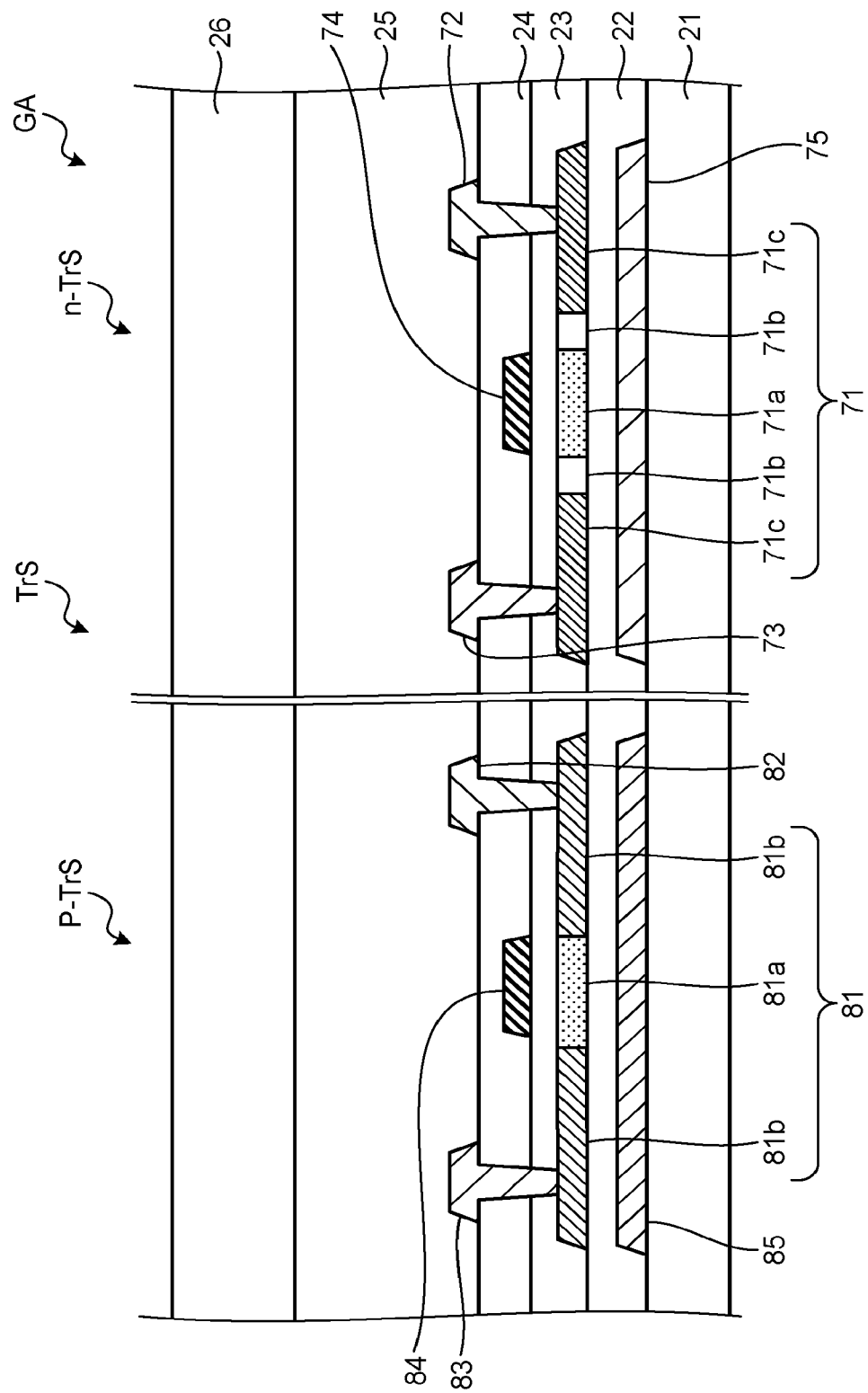
FIG. 12 is a sectional view illustrating a schematic sectional configuration of a switching element included in a drive circuit.

The following describes a stacking configuration of the third switching element TrS. FIG. 12 is a sectional view illustrating a schematic sectional configuration of the switching element included in the drive circuit. FIG. 12 explains the third switching element TrS included as a drive circuit switching element in the signal line selection circuit 16. However, the explanation of FIG. 12 can also be applied to switching elements included in other drive circuits. That is, the same configuration as that of FIG. 12 can be applied to the second switching elements TrG included in the gate line drive circuit 15 and the fourth switching element TrR included in the reset circuit 17.

As illustrated in FIG. 12, the n-channel transistor n-TrS of the third switching element TrS includes a fourth semiconductor layer 71, a source electrode 72, a drain electrode 73, and a gate electrode 74. The p-channel transistor p-TrS includes a fifth semiconductor layer 81, a source electrode 82, a drain electrode 83, and a gate electrode 84. A light-blocking layer 75 is provided between the fourth semiconductor layer 71 and the insulating substrate 21. A light-blocking layer 85 is provided between the fifth semiconductor layer 81 and the insulating substrate 21.

Both the fourth semiconductor layer 71 and the fifth semiconductor layer 81 are of polysilicon. The fourth semiconductor layer 71 and the fifth semiconductor layer 81 are more preferably of LTPS. The fourth semiconductor layer 71 includes an i region 71a, LDD regions 71b, and the n regions 61c. The fifth semiconductor layer 81 includes an i region 81a and p regions 81b.

The n-channel transistor n-TrS and the p-channel transistor p-TrS have the same layer configuration as that of the first switching element Tr illustrated in FIG. 8. That is, the fourth semiconductor layer 71 and the fifth semiconductor layer 81 are provided in the same layer as those of the second semiconductor layer 51 and the third semiconductor layer 61 illustrated in FIG. 8; the gate electrode 74 and the gate electrode 84 are provided in the same layer as those of the gate electrodes 64 illustrated in FIG. 8; and the source electrode 72, the drain electrode 73, the source electrode 82, and the drain electrode 83 are provided in the same layer as those of the source electrode (first relay electrode 56) and the drain electrode 63 (signal line SGL) illustrated in FIG. 8.

As described above, the first photodiode PD1 and the first switching element Tr provided in the detection area AA use the same material and are provided in the same layer as the switching elements are, such as the third switching element TrS provided in the peripheral area GA. This configuration can simplify the manufacturing process and reduce the manufacturing cost of the biological information detection device 1. The drive circuit provided in the peripheral area GA is not limited to being constituted by the CMOS transistor, and may be constituted by either the n-channel transistor n-TrS or the p-channel transistor p-TrS.

Method for Authentication

The detection device 100 has the above-described configuration. The following describes a method for authentication of a user by the controller 6.

Figure 13:
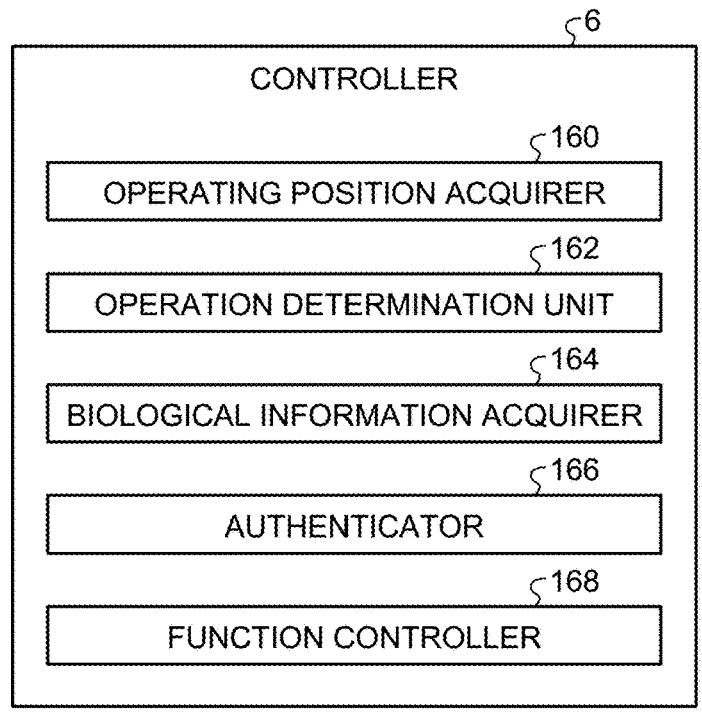
FIG. 13 is a block diagram of a controller according to the embodiment.

FIG. 13 is a block diagram of a controller according to the present embodiment. As illustrated in FIG. 13, the controller 6 includes an operating position acquirer 160, an operation determination unit 162, a biological information acquirer 164, an authenticator 166, and a function controller 168. The controller 6 reads software (computer program) from the storage 8 to implement the operating position acquirer 160, the operation determination unit 162, the biological information acquirer 164, the authenticator 166, and the function controller 168, and executes processing described below.

The operating position acquirer 160 acquires the operating position that is a position on the touchscreen panel 102 where the user has performed an operation. The operating position is detected by the position sensor 10A as described above. The operating position acquirer 160 acquires the information on the operating position from the position sensor 10A. The operating position acquirer 160 acquires the information on the operating position at predetermined intervals of time, that is, the information on the proximity position of the finger Fg or the palm of the user at predetermined intervals of time. The detection of the operating position may be performed by the coordinate extractor 45 of the detector 40 of the biological information acquiring device.

Figure 14:
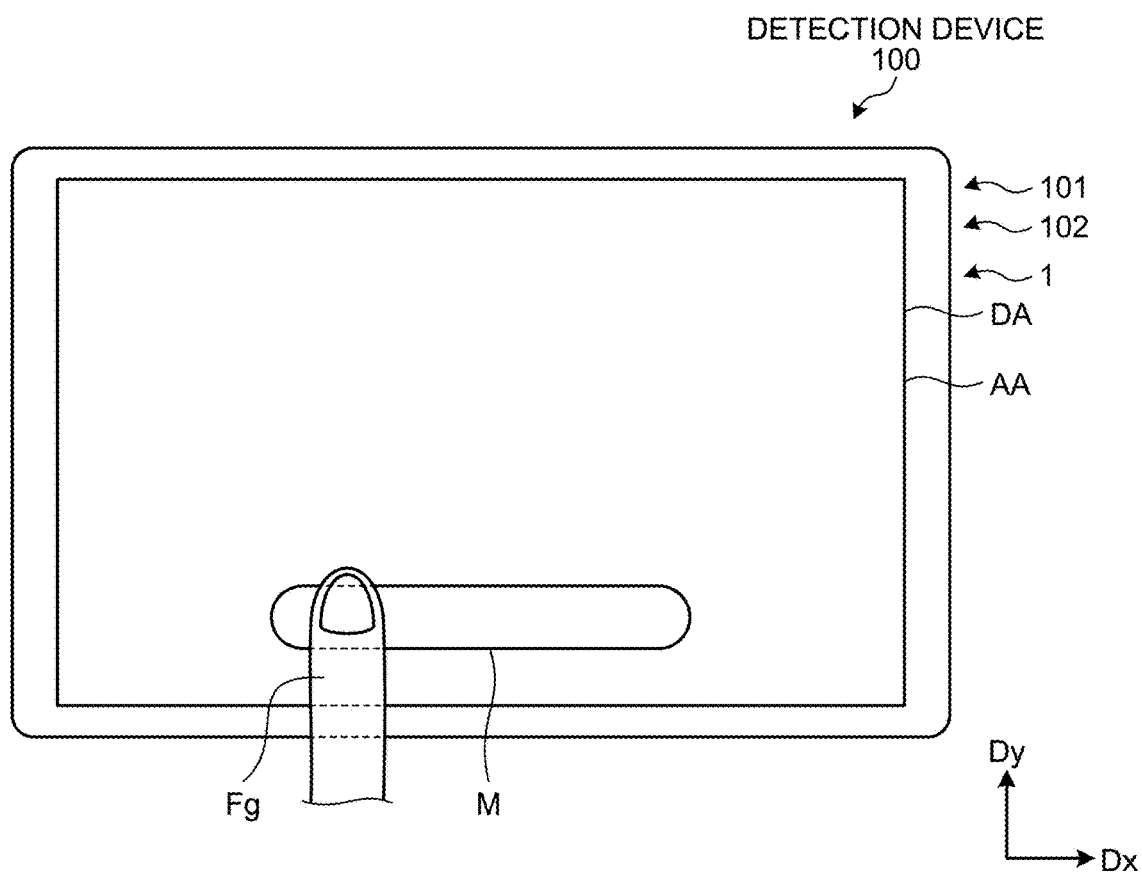
FIG. 14 is a schematic diagram explaining an exemplary trajectory of an operating position.

The operation determination unit 162 determines whether the user operates the touchscreen panel 102 along a predetermined trajectory based on the operating position detected by the position sensor 10A, that is, the operating position acquired by the operating position acquirer 160. Herein, the term "trajectory" refers to a trajectory along which the operating position moves when the operating position, that is, the position on the touchscreen panel 102 to which the user has brought the finger Fg or the palm into proximity continuously moves over time. FIG. 14 is a schematic diagram explaining an exemplary trajectory of the operating position. As illustrated in FIG. 14, a trajectory M of the operating position has a predetermined length obtained by tracing the operating position continuously moving over time on the touchscreen panel 102, more specifically, in the display area DA or above the display area DA overlapping the surface of the touchscreen panel 102. Naturally, the coordinate extractor 45 of the detector 40 of the biological information acquiring device may detect the above-described trajectory M of the operating position.

The operation determination unit 162 determines whether the operating position is continuously moving over time, that is, whether the operating position is used to draw the trajectory M, and in addition, determines whether the trajectory M is a predetermined trajectory set in advance. In the present embodiment, the trajectory M when the operating positions are moving over time in a plurality of directions different from one another, is set as the predetermined trajectory. That is, when the operating positions are continuously moving over time in a plurality of directions different from one another, the operation determination unit 162 determines that the operating positions are used to draw the predetermined trajectory and the user is operating the touchscreen panel 102 along the predetermined trajectory. When, in contrast, the operating positions are not continuously moving over time in a plurality of directions different from one another, the operation determination unit 162 determines that the operating positions are not used to draw the predetermined trajectory and the user is not operating the touchscreen panel 102 along the predetermined trajectory. For example, a pinch-out operation corresponds to this operation, that is, the operation on the touchscreen panel 102 along the predetermined trajectory. The display device is not limited to displaying the predetermined trajectory to cause the user to make the operation along the predetermined trajectory, and may only instruct the user to perform a predetermined operation such as the pinch-out operation or a slide operation.

Figure 15:
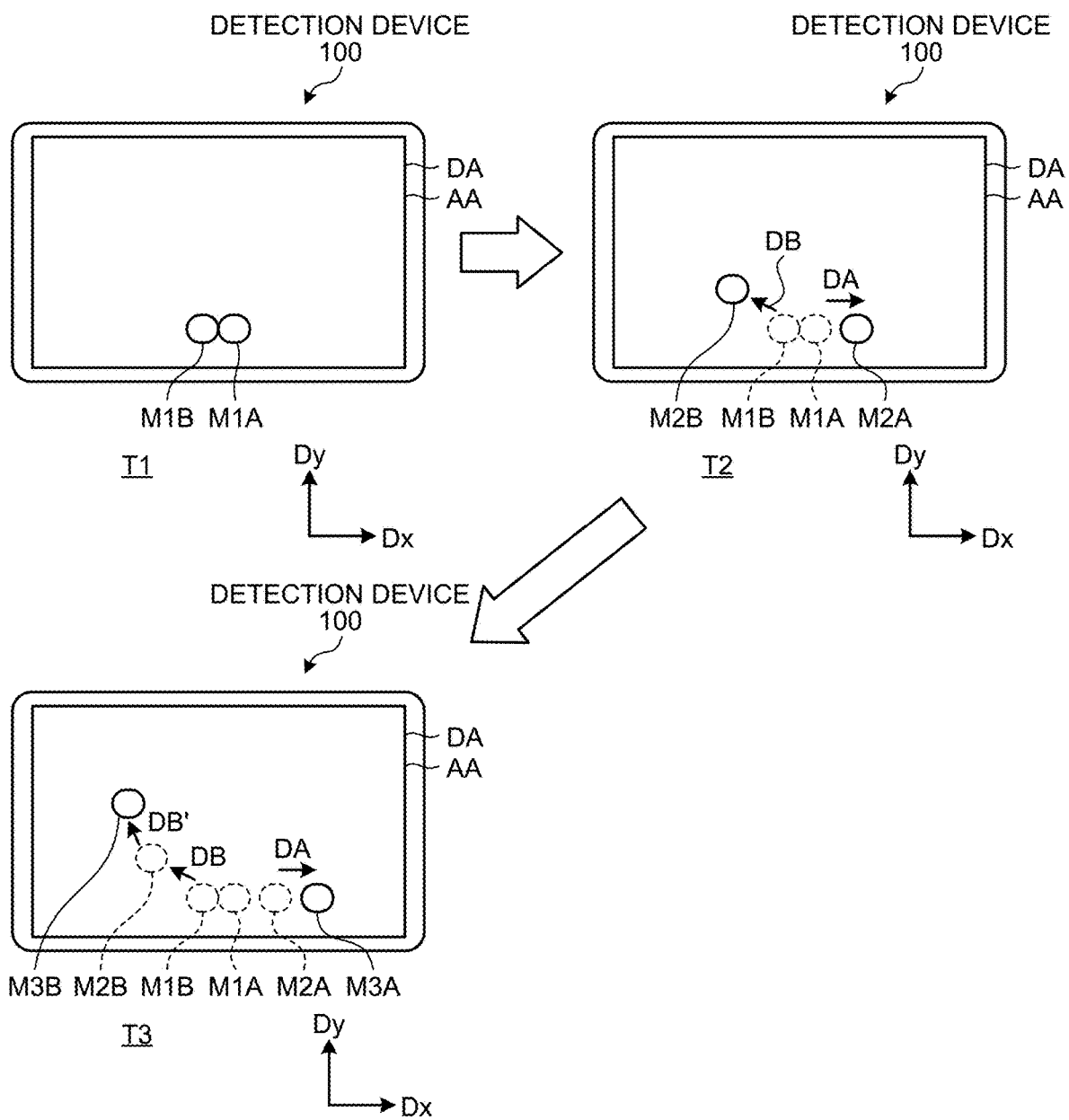
FIG. 15 is a schematic diagram explaining exemplary trajectories of the operating positions.

FIG. 15 is a schematic diagram explaining exemplary trajectories of the operating positions. FIG. 15 illustrates an exemplary case where the operating positions continuously move over time in a plurality of directions different from one another. In the example of FIG. 15, the operating positions at first time T1 are operating positions M1A and M1B. The operating positions at second time T2 after first time T1 are operating positions M2A and M2B. The operating position M2A is located on a direction DA side from the operating position M1A. The operating position M2B is located on a direction DB side from the operating position M1B, the direction DB being different from the direction DA. The operating positions at third time T3 after second time T2 are operating positions M3A and M3B. The operating position M3A is located on the direction DA side from the operating position M2A. The operating position M3B is located on the direction DB side from the operating position M2B, the direction DB being different from the direction DA. In this case, the trajectory M of the operating positions is obtained by moving the operating positions in directions different from each other, that is, in the direction DA of moving from the operating position M1A via the operating position M2A to the operating position M3A and in a direction DB' of moving from the operating position M1B via the operating position M2B to the operating position M3B. If the operating positions are moving, for example, as illustrated in FIG. 15, the operation determination unit 162 determines that the operating positions are used to draw the predetermined trajectory. FIG. 15 illustrates a mere example of the predetermined trajectory. The operation determination unit 162 in the present embodiment only needs to determine that the operating positions are used to draw the predetermined trajectory if the operating positions are continuously moving in a plurality of directions different from one another. For example, in FIG. 15, the operating position is continuously moving in the same direction DA from the operating position M1A via the operating position M2A to the operating position M3A. However, the movement direction may change over time. The operation determination unit 162 only needs to determine that the predetermined positions are drawn if the operating positions are moving in a plurality of different directions at the same time (for example, if the direction from the operating position M1A to the operating position M2A differs from the direction from the operating position M1B to the operating position M2B). In the example of FIG. 15, the operating positions move in two different directions at the same time. However, the operating positions may move in three or more different directions.

The predetermined trajectory is not limited to that obtained by the operating positions continuously moving over time in a plurality of directions different from one another, and can be set freely. For example, if the operating position is continuously moving over time by a predetermined length or longer (for example, if the user is performing a slide operation on the screen with at least one finger Fg as illustrated in FIG. 14), the operation determination unit 162 may determine that the predetermined trajectory is drawn.

Referring back to FIG. 13, the biological information acquirer 164 acquires the biological information on the user (such as the fingerprint and the vascular pattern) from the biosensor 10. Specifically, as described above, the biosensor 10 outputs the detection signals Vdet corresponding to the light L2 reflected by the finger Fg or the palm of the user in proximity to the touchscreen panel 102 through the signal line selection circuit 16 (refer to FIG. 3) to the detector 40 (refer to FIG. 3). The detector 40 causes the coordinate extractor 45 to generate the biological information on the user (herein, the two-dimensional information on the fingerprint and the vascular pattern) based on the detection signals Vdet. The biological information acquirer 164 acquires the biological information on the user from the detector 40.

In more detail, if the operation determination unit 162 determines that the operating position has been used to draw the predetermined trajectory, the biological information acquirer 164 acquires the biological information on the user in the operating position that has been used to draw the predetermined trajectory. In other words, if the operation determination unit 162 determines that the user has operated the touchscreen panel 102 along the predetermined trajectory, the biological information acquirer 164 acquires, from the biosensor 10, the biological information on the user when the user has operated the touchscreen panel 102 along the predetermined trajectory. That is, at the time when the predetermined trajectory has been drawn, the biological information acquirer 164 acquires, from the biosensor 10, the biological information on the user in the operating position that has been used to draw the predetermined trajectory.

Since the predetermined trajectory is obtained by tracing the operating position, a plurality of the operating positions are present that have been used to draw the predetermined trajectories. The biological information acquirer 164 may acquire the biological information on the user in all the operating positions that have been used to draw the predetermined trajectories, or may acquire the biological information on the user in some of the operating positions. When the biological information acquirer 164 acquires the biological information on the user in some of the operating positions, the biological information acquirer 164 may acquire the biological information in the operating positions detected at later times. That is, in the example of FIG. 15, the biological information acquirer 164 may acquire the biological information in the operating positions M2A, M2B, M3A, and M3B detected at later times or the biological information in the operating positions M3A and M3B detected at the latest time, among the operating positions M1A, M1B, M2A, M2B, M3A, and M3B. The predetermined trajectories are obtained by tracing the respective operating positions when the operating positions are moving in a plurality of directions. Accordingly, the operating positions are detected at the same time. In this case, the biological information acquirer 164 may acquire the biological information in all the operating positions (for example, the biological information in both the operating positions M3A (of, for example, the thumb of the left hand of the user) and M3B (of, for example, the index finger of the left hand of the user)), or may acquire the biological information in some of the operating positions (for example, the biological information in one of the operating positions M3A and M3B), among the operating positions at the same time. When the user traces the above-described trajectory on the screen, the angle of the finger of the user changes with respect to the biological information acquirer 164. Therefore, the biological information acquirer 164 may select, from among a plurality of pieces of the biological information on the user in the operating positions, the most clearly acquired biological information, or the biological information on the user with an angle exactly or approximately equal to a predetermined angle between the finger of the user and the biological information acquirer 164, as the biological information on the user. This function may be performed by the arithmetic device of the electronic apparatus coupled to the detection device 100.

The authenticator 166 determines, based on the biological information on the user acquired by the biological information acquirer 164, whether to execute the predetermined function. As described above, the predetermined function is, for example, a function required by the user to be executed by the detection device 100 (for example, starting a computer program or access to a website). The authenticator 166 reads the reference biological information that is the biological information serving as a reference stored in advance from the storage 8. The reference biological information is stored in advance as, for example, the biological information on the user (herein, the two-dimensional information on the fingerprint and the vascular pattern) allowed to use the predetermined function. The reference biological information is not limited to being stored in the storage 8, and may be acquired, for example, from an external device through communication. The authenticator 166 checks for a match between the biological information on the user and the reference biological information to determine whether the biological information on the user matches with the reference biological information. For example, the authenticator 166 may check for a pattern match between the biological information on the user and the reference biological information, and may determine that the biological information on the user matches with the reference biological information if the degree of similarity of feature points is equal to or higher than a predetermined degree, or determine that the biological information on the user does not match with the reference biological information if the degree of similarity is lower than the predetermined degree. A known technique may be used to check for a match between the biological information on the user and the reference biological information.

If the authenticator 166 determines that the biological information on the user matches with the reference biological information, the authenticator 166 determines that the user has been authenticated, and determines to execute the predetermined function. If, instead, the authenticator 166 determines that the biological information on the user does not match with the reference biological information, the authenticator 166 determines that the user cannot be authenticated, and determines not to execute the predetermined function.

The function controller 168 controls the detection device 100 to cause the detection device 100 to execute the predetermined function. The function controller 168 causes the detection device 100 to execute the predetermined function if the authenticator 166 determines to execute the predetermined function, that is, determines that the user has been authenticated. The function controller 168 does not cause the detection device 100 to execute the predetermined function if the authenticator 166 determines not to execute the predetermined function, that is, determines that the user cannot be authenticated.

When the operating positions of the user have been used to draw the predetermined trajectory as described above, the controller 6 acquires the biological information on the user and performs the authentication to determine whether to execute the predetermined function. If the area of contact of the finger Fg with the touchscreen panel 102 is small or the time of contact thereof is short, the biological information may not be appropriately detected, and thus, accuracy of the authentication may be reduced. However, the detection device 100 according to the present embodiment acquires the biological information when the predetermined trajectory has been drawn. Therefore, the accuracy of the authentication can be restrained from decreasing by appropriately detecting the biological information on the user. That is, when the predetermined trajectory has been drawn, the time of contact and the area of contact of the finger Fg with the touchscreen panel 102 tend to be larger. Therefore, the biological information on the user can be appropriately detected by acquiring the biological information when the predetermined trajectory has been drawn.

Figure 16:
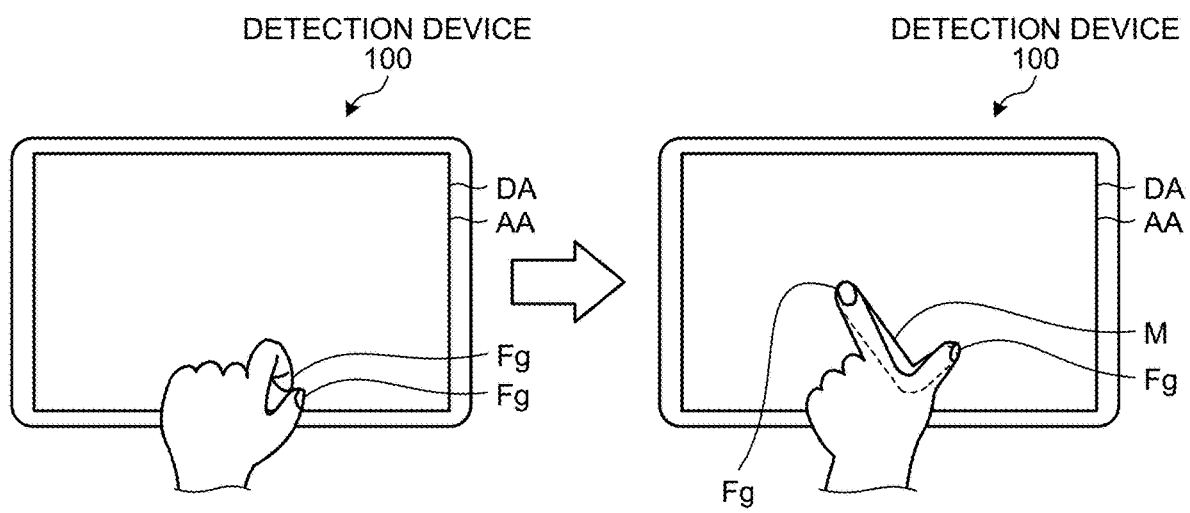
FIG. 16 is a schematic diagram illustrating an exemplary operation of a user.

In addition, in the present embodiment, the predetermined trajectory refers to the trajectory along which the operating positions move in a plurality of directions different from one another. When the predetermined trajectory is drawn as described above, the user is likely to be performing the pinch-out operation to operate the touchscreen panel 102. FIG. 16 is a schematic diagram illustrating an exemplary operation of the user. As illustrated in the example of FIG. 16, the term "pinch-out" refers to an operation of moving a plurality of the fingers Fg away from one another. When the pinch-out operation is performed as described above, the operating positions that are positions in proximity to the fingers Fg form the trajectory M along which the operating positions move in a plurality of directions different from one another. When the user performs the pinch-out operation in this manner, the ball of the finger Fg contacts the touchscreen panel 102. As a result, the area of contact of the finger Fg with the touchscreen panel 102 is larger than that of, for example, a fingertip when contacting the touchscreen panel 102. That is, the detection device 100 acquires the biological information in the case of the predetermined trajectory, particularly when the pinch-out operation is performed. Thereby, the detection device 100 can acquire the biological information in the case where the area of contact of the finger Fg with the touchscreen panel 102 is larger, and thus, can appropriately detect the biological information on the user. In particular, to increase the accuracy of detection of the vascular pattern, the area of contact of the finger Fg with the touchscreen panel 102 is preferably larger. Therefore, the detection device 100 according to the present embodiment can suitably detect the vascular pattern.

In the present embodiment, the detection device 100 causes the authenticator 166 to perform the authentication. However, the detection device 100 need not perform the authentication. In this case, for example, the controller 6 transmits the acquired biological information on the user to another device, and the other device may act as the authenticator 166 to perform the authentication by checking for a match between the biological information on the user and the reference biological information. Then, the other device transmits the result of the authentication, that is, the result of the determination on whether to execute the predetermined function to the detection device 100, and the detection device 100 determines, based on the result of the determination, whether to execute the predetermined function.

Figure 17:
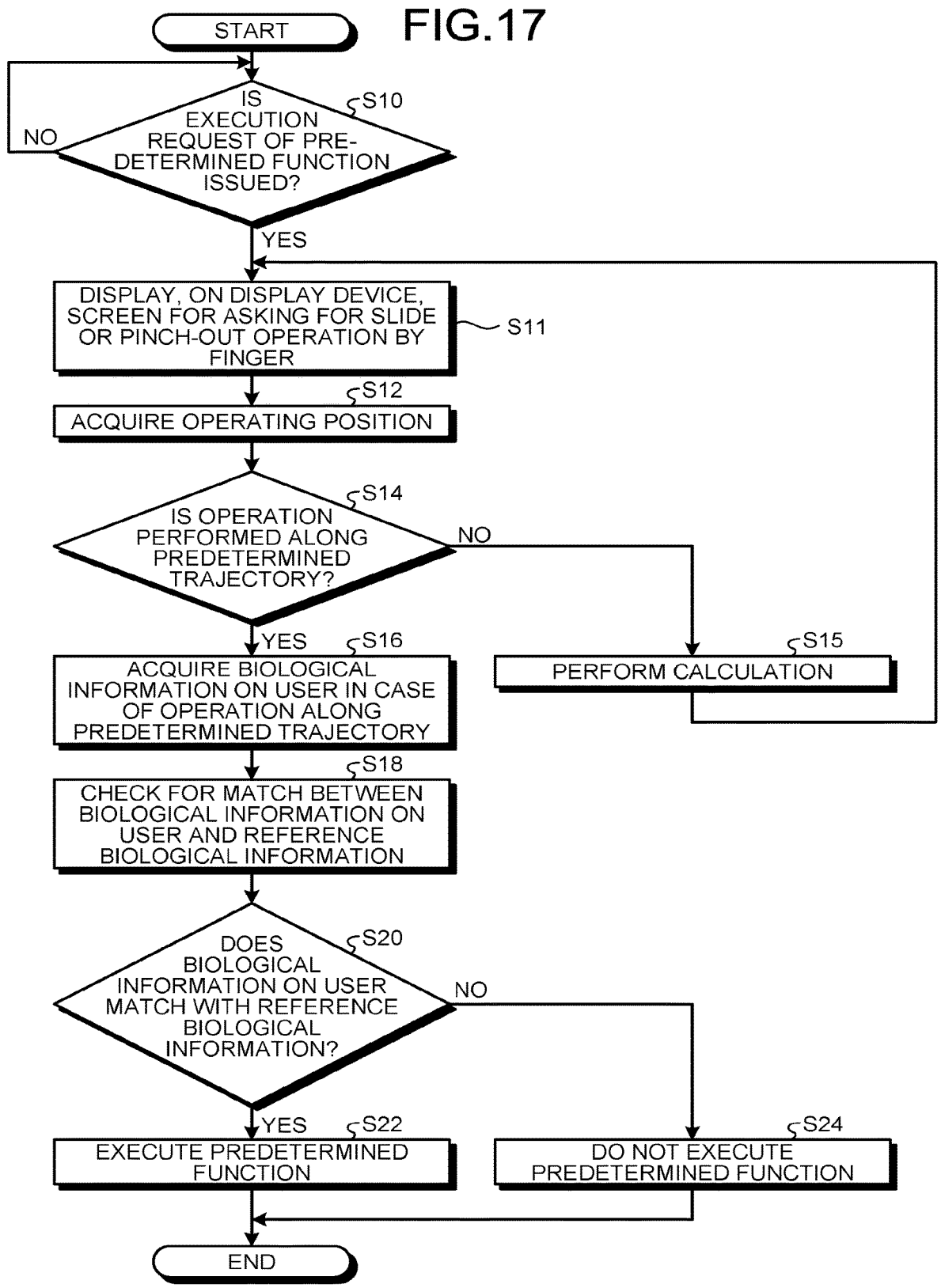
FIG. 17 is a flowchart explaining authentication processing according to the embodiment.

The following describes a flow of authentication processing based on a flowchart. FIG. 17 is the flowchart explaining the authentication processing according to the embodiment. As illustrated in FIG. 17, the detection device 100 determines whether an execution request of the predetermined function is issued (Step S10). The detection device 100 causes, for example, the controller 6 to determine whether the detection device 100 is requested to execute the predetermined function. The execution request of the predetermined function is issued to the detection device 100 by an operation of the user, that is, by an operation in which the user operates the input unit (for example, the touchscreen panel 102) of the detection device 100 for executing the predetermined function. However, the execution request of the predetermined function is not limited to being issued by the operation of the user as a trigger, and may be, for example, automatically issued at predetermined intervals of time. The trigger may be issued when the user comes close to the device if the detection device 100 is incorporated in an electronic apparatus such as the entrance management apparatus, or may be issued when the user inserts a card or the like into the electronic apparatus if the detection device 100 is incorporated in an electronic apparatus such as the ATM.

If the execution request of the predetermined function is issued (Yes at Step S10), the display device (detection device 100) displays a screen for instructing the user to make the finger or the like touch the screen, and slide the finger or perform the pinch-out operation, that is, a guidance image P to be described later (Step S11). The detection device 100 causes the operating position acquirer 160 of the controller 6 to acquire the information on the operating position detected by the position sensor 10A (Step S12). The operating position acquirer 160 acquires the information on the operating position at predetermined intervals of time, that is, the information on the proximity position of the finger Fg or the palm of the user at predetermined intervals of time. If the execution request of the predetermined function is not issued (No at Step S10), the process returns to Step S10, and the detection device 100 continues to determine whether the execution request of the predetermined function is issued.

After the information on the operating position is acquired, the detection device 100 causes the operation determination unit 162 of the controller 6 to determine whether the user has operated the touchscreen panel 102 along the predetermined trajectory (Step S14). The operation determination unit 162 determines, based on the information on the operating position at predetermined intervals of time, whether the operating position is continuously moving so as to draw the predetermined trajectory. If the detection device 100 determines that the user has operated the touchscreen panel 102 along the predetermined trajectory (Yes at Step S14), the detection device 100 causes the biological information acquirer 164 of the controller 6 to acquire the biological information on the user when the user has operated the touchscreen panel 102 along the predetermined trajectory (Step S16). If the detection device 100 determines that the user has not operated the touchscreen panel 102 along the predetermined trajectory (No at Step S14), the detection device 100 performs, for example, the processing at Step S11 again to display the guidance image P and continues to acquire the operating position. In this case, if sufficient biological information is determined to be not acquirable through the instruction displayed on the display device due to, for example, the size of the hand of the user, the detection device 100 can perform calculation to change, for example, the distance, angle, or time of the slide operation or the distance, angle, or time of the pinch-out operation displayed on the display device, and can reflect the change in the display used when acquiring the biological information again. For example, the biological information can be accurately acquired by reducing the distance of the pinch-out operation if the finger is determined to be shorter than expected, or by increasing the distance of the pinch-out operation if the finger is determined to be longer than expected. That is, if the detection device 100 determines that the user has not operated the touchscreen panel 102 along the predetermined trajectory (No at Step S14), the detection device 100 performs the calculation to display the guidance image P again (Step S15), and performs the processing at Step S11 again to display the screen based on the performed calculation. That is, the detection device 100 may perform calculation based on the information on the operating position used when the touchscreen panel 102 is determined to be not operated along the predetermined trajectory, and change the display content of the next guidance image P from the display content of the previous guidance image P based on the calculation. This calculation can be said as calculation to change the guidance image P to an image that further facilitates the operation by the user along the predetermined trajectory. The slide and pinch-out operations of the finger of the user may be independently displayed for acquiring the biological information, but may be integrated with display of a button used when a predetermined application displayed on a home screen is started, or display of a "Withdraw" button in the case of the ATM.

After the biological information on the user in the case of the predetermined trajectory is acquired, the detection device 100 causes the authenticator 166 of the controller 6 to check for a match between the biological information on the user and the reference biological information (Step S18). If the biological information on the user matches with the reference biological information (Yes at Step S20), the detection device 100 determines that the user has been authenticated and the predetermined function may be executed, and causes the function controller 168 to execute the predetermined function (Step S22). If the biological information on the user does not match with the reference biological information (No at Step S20), the user is determined to be not authenticated, and the predetermined function is not executed (Step S24). This process ends after Step S22 or Step S24. However, even if the user is determined to be not authenticated, the process may return to for example, Step S11 or Step S16 to continue the authentication processing again if this process has been performed for the first time. In that case, the process may return to Step S15 to perform the calculation described above. If the user is determined to be not authenticated (No at Step S20) for the second time, the process may go to Step S24. Even after the user is determined to be authenticated and the processing at Step S22 is performed, the process may return to for example, Step S11 or Step S16 to continue to perform the authentication processing at predetermined intervals of time.

The biological information acquirer 164 in the present embodiment acquires the biological information if the trajectory is determined to be the predetermined trajectory. However, the biological information acquirer 164 may leave the biological information unacquired from the biosensor 10 until the trajectory is determined to be the predetermined trajectory, and may acquire the biological information from the biosensor 10 by being triggered when the trajectory is determined to be the predetermined trajectory. The biological information acquirer 164 may always acquire the biological information from the biosensor 10 regardless of the determination on whether the trajectory is the predetermined trajectory. In this case, the biological information acquirer 164 may store in advance the biological information acquired from the biosensor 10 in, for example, the storage 8, and the biological information acquirer 164 may read to acquire the biological information corresponding to the operating position that has been used to draw the predetermined trajectory from the storage 8 by being triggered when the trajectory of the operating position is determined to be the predetermined trajectory, and use the acquired biological information for the authentication. In the present embodiment, the biosensor 10 is driven to detect the biological information by being triggered when the execution request of the predetermined function is issued as described as Step S10. However, the biosensor 10 is not limited to being driven by being triggered in this manner, and may be always driven, or may be driven by being triggered, for example, when the position sensor 10A detects the proximity.

As described above, the detection device 100 according to the present embodiment includes the input unit (herein, the touchscreen panel 102) for receiving operations of the user, the biosensor 10 that is provided on the input unit and detects the biological information on the user, the position sensor 10A that detects the operating position that is a position on the input unit where the user has performed an operation, and the controller 6. The controller 6 includes the operation determination unit 162 and the biological information acquirer 164. The operation determination unit 162 determines, based on the operating position detected by the position sensor 10A, whether the user has operated the input unit along the predetermined trajectory. If the user is determined to have operated the input unit along the predetermined trajectory, the biological information acquirer 164 acquires, from the biosensor 10, the biological information on the user when the user has operated the input unit along the predetermined trajectory. This detection device 100 acquires the biological information when the predetermined trajectory has been drawn. As a result, the biological information on the user can be appropriately detected by increasing the time of proximity and the area of contact of the user to the touchscreen panel 102.

The controller 6 further includes the authenticator 166 that determines, based on the acquired biological information on the user, whether to execute the predetermined function specified in advance. This detection device 100 can cause the authenticator 166 to appropriately perform the user authentication.

The operation determination unit 162 determines, based on the operating positions, whether the user has performed the pinch-out operation of moving a plurality of fingers away from one another. If the user is determined to have performed the pinch-out operation, the operation determination unit 162 determines that the user has operated the input unit along the predetermined trajectory. When the user performs the pinch-out operation, the area of contact of the finger Fg tends to be larger. Accordingly, the detection device 100 can appropriately detect the biological information on the user by acquiring the biological information on the assumption that the user is drawing the predetermined trajectory when performing the pinch-out operation.

The biosensor 10 detects at least one of the vascular pattern of the user and the fingerprint of the user. This detection device 100 can appropriately perform the authentication of the user by detecting the vascular pattern and/or the fingerprint as the biological information.

The biosensor 10 includes the semiconductor (first semiconductor layer 31) containing amorphous silicon and the semiconductor (second semiconductor layer 51) containing polysilicon, and detects the vascular pattern of the user and the fingerprint of the user. By including such a biosensor 10, the detection device 100 can perform the authentication based on a plurality of types of the biological information, and thus, can increase the accuracy of the authentication. For example, the detection device 100 may determine that the user has been authenticated and execute the predetermined function if both the fingerprint and the vascular pattern of the user match with those of the reference biological information. Alternatively, the detection device 100 may acquire one of the fingerprint and the vascular pattern of the user, and, if the acquired one matches with the reference biological information, may determine that the user has been authenticated and execute the predetermined function. The detection device 100 may then acquire the other of the fingerprint and the vascular pattern of the user, and may halt the execution of the predetermined function if the other does not match with the reference biological information. Visible light is used to detect the fingerprint, and infrared light is used to detect the vascular pattern. For example, in the initial stage of the pinch-out operation, the infrared light may be used to acquire the vascular pattern, and when the fingers are sufficiently parallel to the detection device 100 in the final stage of the pinch-out operation, the fingerprint or both the fingerprint and the vascular pattern may be acquired. When the display device and the detection device are formed to have the same size, the biological information can be detected at any part of the screen of the display device. However, when the detection device is disposed only in a portion of the display device, the display device may be caused to display a screen for aligning an endpoint of the slide operation or an endpoint of the pinch-out operation with the detection device.

Figure 18:
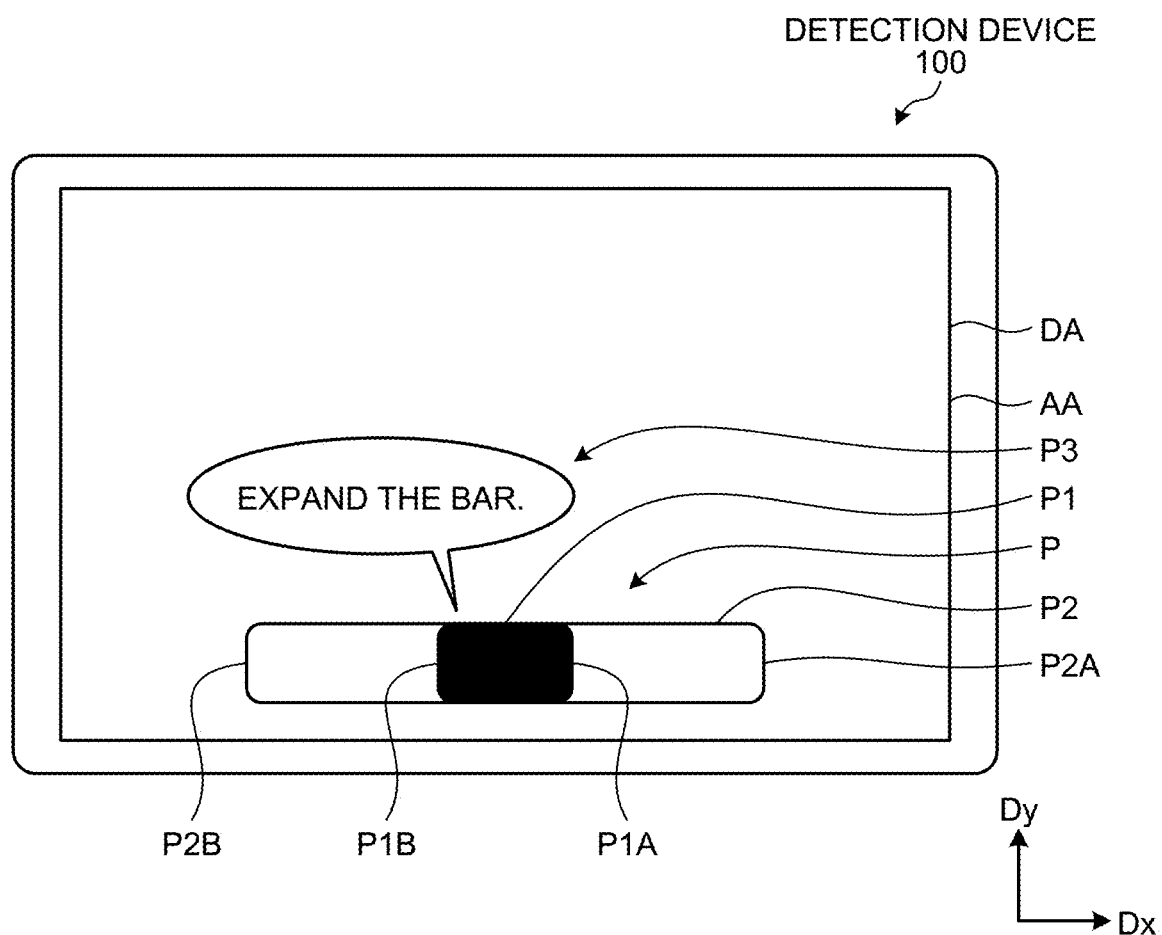
FIG. 18 is a diagram illustrating an exemplary guidance image.

The detection device 100 may cause the display panel 101 to display the guidance image P serving as an image for guiding the operation of the touchscreen panel 102 along the predetermined trajectory. FIG. 18 is a diagram illustrating an example of the guidance image. The detection device 100 causes, for example, the controller 6 to display the guidance image P in the display area DA of the display panel 101. In the example of FIG. 18, the guidance image P includes images P1, P2, and P3. The images P1 and P2 are bar-shaped images. The image P1 is displayed in the center position of the image P2 in the area of the image P2. That is, assuming that the image P1 is an image extending from one end P1A to another end P1B and the image P2 is an image extending from one end P2A to another end P2B, the one end P1A of the image P1 is located closer to the other ends P2A and P2B than the one end P2A of the image P2 is (the opposite side of the one end P2A in the first direction Dx in the example of FIG. 18), and the other end P1B of the image P1 is located closer to the one ends P1A and P2A than the other end P2B of the image P2 is (the other end P2B side in the first direction Dx in the example of FIG. 18). The image P3 is displayed with a notification prompting the user to expand the image P1.

Displaying the guidance image P guides the user to operate the touchscreen panel 102 so as to expand the image P1 toward both sides. When the touchscreen panel 102 is operated so as to expand the image P1 toward both sides, in the guidance image P, the one end P1A of the image P1 moves to expand the image P1 toward the one end P2A of the image P2, and the other end P2A of the image P1 moves to expand the image P1 toward the other end P2B of the image P2. When the touchscreen panel 102 is operated to expand the image P1 toward both sides in this manner, the operating positions move in a plurality of different directions to draw the predetermined trajectory, in other words, the trajectory obtained when the user performs the pinch-out operation. Since the operating positions are used to draw the predetermined trajectory in this manner, the detection device 100 can detect the biological information.

As described above, the detection device 100 includes the display panel 101 that is provided so as to overlap the input unit (touchscreen panel 102) and displays an image. The controller 6 may cause the display panel 101 to display the guidance image P for guiding the user to operate the input unit along the predetermined trajectory. This detection device 100 increases the probability for the user to operate the input unit along the predetermined trajectory, and thus, can suitably detect the biological information. The guidance image P is not limited to the example in FIG. 18, and may be any guidance image.

Other operational advantages accruing from the aspects described in the embodiment of the present invention that are obvious from the description herein, or that are conceivable as appropriate by those skilled in the art will naturally be understood as accruing from the present invention.

What is claimed is:

1. A detection device comprising:
a touchscreen panel configured to receive an operation of a user;
a biosensor provided on the touchscreen panel and configured to detect biological information on the user;
a position sensor configured to detect an operating position that is a position on the touchscreen panel where the user has performed the operation; and
a controller, wherein
the controller comprises:
an operation determination controller configured to determine, based on the operating position detected by the position sensor, whether the user has operated the touchscreen panel along a predetermined trajectory;
a biological information acquirer controller configured to, when the user is determined to have operated the touchscreen panel along the predetermined trajectory, acquire, from the biosensor, the biological information on the user when the user has operated the touchscreen panel along the predetermined trajectory; and
an authenticator controller configured to determine, based on the acquired biological information on the user, whether to execute a predetermined function,
wherein the biological information acquirer controller acquires the biological information in the operating position detected at a latest time among the predetermined trajectory,
the authenticator controller determines, based on the biological information in the operating position detected at the latest time, whether to execute the predetermined function,
the biosensor comprises a semiconductor containing amorphous silicon and a semiconductor containing polysilicon, and is configured to detect a vascular pattern of the user and a fingerprint of the user,
the biological information acquirer controller acquires, as the biological information, the vascular pattern detected in an initial stage of the predetermined trajectory and the fingerprint and the vascular pattern detected in a final stage of the predetermined trajectory, and
the authenticator controller determines, based on the vascular pattern detected in the initial stage of the predetermined trajectory and the fingerprint and the vascular pattern detected in the final stage of the predetermined trajectory, whether to execute the predetermined function.

2. The detection device according to claim 1, further comprising a display provided so as to overlap the touchscreen panel and configured to display an image, wherein
the controller is configured to cause the display to display an image for guiding to operate the touchscreen panel along the predetermined trajectory.

3. The detection device according to claim 1, wherein the operation determination controller is configured to determine, based on the operating position, whether the user has performed a pinch-out operation of moving a plurality of fingers away from one another, and determine that the touchscreen panel has been operated along the predetermined trajectory when the user is determined to have performed the pinch-out operation.

* * * * *